United States Patent
Matsuo et al.

(10) Patent No.: US 10,287,419 B2
(45) Date of Patent: May 14, 2019

(54) RUBBER COMPOSITION AND VULCANIZATION AID

(71) Applicant: SUMITOMO CHEMICAL COMPANY, LIMITED, Tokyo (JP)

(72) Inventors: Kazumasa Matsuo, Osaka (JP); Orhan Ozturk, Tokyo (JP); Yasuo Uekita, Osaka (JP)

(73) Assignee: SUMITOMO CHEMICAL COMPANY, LIMITED, Chuo-ku, Tokyo (JP)

( * ) Notice: Subject to any disclaimer, the term of this patent is extended or adjusted under 35 U.S.C. 154(b) by 329 days.

(21) Appl. No.: 15/038,904

(22) PCT Filed: Nov. 26, 2014

(86) PCT No.: PCT/JP2014/081215
§ 371 (c)(1),
(2) Date: May 24, 2016

(87) PCT Pub. No.: WO2015/080144
PCT Pub. Date: Jun. 4, 2015

(65) Prior Publication Data
US 2017/0130028 A1    May 11, 2017

(30) Foreign Application Priority Data

Nov. 26, 2013 (JP) ................................. 2013-243590

(51) Int. Cl.
| | |
|---|---|
| B60C 1/00 | (2006.01) |
| C07D 213/70 | (2006.01) |
| C07D 213/89 | (2006.01) |
| C08K 3/06 | (2006.01) |
| C08K 5/00 | (2006.01) |
| C08K 5/34 | (2006.01) |
| C08K 5/3432 | (2006.01) |
| C08K 5/36 | (2006.01) |
| C08K 5/43 | (2006.01) |
| C08K 5/47 | (2006.01) |

(52) U.S. Cl.
CPC .............. C08K 5/3432 (2013.01); B60C 1/00 (2013.01); C07D 213/70 (2013.01); C07D 213/89 (2013.01); C08K 3/06 (2013.01); C08K 5/0025 (2013.01); C08K 5/34 (2013.01); C08K 5/36 (2013.01); C08K 5/43 (2013.01); C08K 5/47 (2013.01)

(58) Field of Classification Search
CPC .......... C08K 5/3432; C08K 5/34; C08K 5/36; C08K 5/47; C08K 5/0025; C08K 5/43; C08K 3/06; B60C 1/00; C07D 213/89; C07D 213/70
See application file for complete search history.

(56) References Cited

U.S. PATENT DOCUMENTS

| | | | |
|---|---|---|---|
| 1,356,495 A | 10/1920 | Winfield | |
| 4,761,446 A | 8/1988 | Graves et al. | |
| 5,256,532 A | 10/1993 | Melnicoff et al. | |
| 5,324,775 A | 6/1994 | Rhee et al. | |
| 5,623,007 A | 4/1997 | Kuebler | |
| 8,680,288 B2 * | 3/2014 | Sarma ................ | C07D 213/70 546/301 |
| 2009/0043014 A1 | 2/2009 | Narita et al. | |
| 2012/0141712 A1 | 6/2012 | Otaka et al. | |
| 2013/0131350 A1 | 5/2013 | Sarma et al. | |

FOREIGN PATENT DOCUMENTS

| | | |
|---|---|---|
| CN | 1074911 A | 8/1993 |
| CN | 102458838 A | 5/2012 |
| CN | 103003242 A | 3/2013 |
| EP | 0 249 328 A2 | 12/1987 |
| EP | 2439067 A1 | 4/2012 |
| JP | 2005-15638 A | 1/2005 |
| JP | 2009-40898 A | 2/2009 |
| WO | 92/13520 A1 | 8/1992 |
| WO | 2010/140583 A1 | 12/2010 |

OTHER PUBLICATIONS

Saraiva et al., "The Barton Ester Free-radical REaction: A Brief Review of Applications", Tetrahedron, 2009, 65, pp. 3563-3572.*
Communication dated Apr. 18, 2018 from the Taiwanese Patent Office in counterpart Taiwanese application No. 103140992.
Zhang et al., "Modern Drug Design", China Medical Science Press, May 2006, p. 116 (total 5 pages).
Communication dated Feb. 11, 2018 from the State Intellectual Property Office of the P.R.C. in counterpart Application No. 201480062819.9.
The Society of Rubber Science and Technology, "Gomu Kogyo Binran (Rubber industrial Handbook) Fourth edition", The Society of Rubber Science and Technology, 1994, pp. 412-413.
(Continued)

*Primary Examiner* — Patrick D Niland
(74) *Attorney, Agent, or Firm* — Sughrue Mion, PLLC

(57) ABSTRACT

A rubber composition comprising a compound having one or more groups represented by formula (X) and a rubber component is provided.

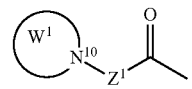

(X)

wherein ring $W^1$ represents a cyclic group having at least one selected from the group consisting of —C(=O)— and —C(=S)—; $N^{10}$ represents a nitrogen atom; the at least one selected from the group consisting of —C(=O)— and —C(=S)— in the ring $W^1$ and $N^{10}$ are conjugated; and $Z^1$ represents —O— or —S—.

13 Claims, No Drawings

(56) References Cited

OTHER PUBLICATIONS

Okano, Takashi et al., "A Facile Preparation Method for α,α-Difluoro-alkanecarboxylic Acids and Esters. A Formal Difluoromethylene Insertion to Alkanecarboxylic Acids Using Radical Reaction", Tetrahedron, 1995, vol. 51, No. 7, pp. 1903-1920.

Poigny, Stèphane et al., "One-step Synthesis of Tyromycin A and Analogues", J. Org. Chem., 1998, vol. 63, pp. 1342-1343.

Okano, Takashi et al., "α,α-Difluoralkanecarboxylic Acids: A General Synthesis via Alkyl Radical Addition to 1,1-Dichloro-2,2-difluoroethylene", Tetrahedron Letters, 1992, vol. 33, No. 24, pp. 3491-3494.

Togo, Hideo, "2,2'-Dipyridyl Disulfide-N,N-Dioxide", e-EROS Encyclopedia of Reagents for Organic Synthesis, 2001, pp. 4610-4613.

P. Margaretha, "Substitution of Carbon Functionalities", Science of Synthesis, 2007, vol. 35, pp. 303-312.

Hartung, Jens et al., "The Use of Propane Phosphonic Acid Anhydride (PPAA) in the Synthesis of N-Acyloxythiazole-2(3H)-thiones", Synlett, 2000, No. 3, pp. 371-373.

Scheumann, Klaus et al., "The Pagodane Route to Dodecahedranes—Functional Group Manipulations on the Dodecahedrane Sphere", Tetrahedron Letters, 1992, vol. 33, No. 5, pp. 615-618.

Romero, F.M. et al., "A Straightforward Synthesis of 5-Bromo and 5,5'-Dibromo-2,2'-Bipyridines", Tetrahedron Letters, 1995, vol. 36, No. 36, pp. 6471-6474.

Theodorakis, E.A. et al., "N-Aroyloxy-2-thiopyridones as efficient oxygen-radical generators: novel time-controlled DNA photocleaving reagents", Chem. Commun., 1996, pp. 1927-1928.

International Search Report dated Feb. 10, 2015, issued by the International Searching Authority in application No. PCT/JP2014/081215.

International Preliminary Report on Patentability dated Jun. 9, 2016, issued by the International Searching Authority in application No. PCT/JP2014/081215.

Communication dated Nov. 30, 2016, from the State Intellectual Property Office of People's Republic of China in counterpart Application No. 201480062819.9.

Communication dated Aug. 7, 2017 from the State Intellectual Property Office of the P.R.C., in counterpart Chinese application No. 201480062819.9.

Communication dated Jul. 3, 2017, issued from the Europe Patent Office in counterpart Application No. 14866635.7.

Fourth Office Action dated Oct. 15, 2018 from the State Intellectual Property Office of the P.R.C. in counterpart Application No. 201480062819.9.

Notice of Reasons for Rejection dated Jan. 8, 2019, from Japanese Patent Office in counterpart application No. 2015-550954.

* cited by examiner

RUBBER COMPOSITION AND VULCANIZATION AID

CROSS REFERENCE TO RELATED APPLICATIONS

This application is a National Stage of International Application No. PCT/JP2014/081215 filed Nov. 26, 2014, claiming priority based on Japanese Patent Application No. 2013-243590, filed Nov. 26, 2013, the contents of all of which are incorporated herein by reference in their entirety.

TECHNICAL FIELD

The present invention relates to a rubber composition and a vulcanization aid.

BACKGROUND ART

As vulcanization aids, thiazole-based vulcanization accelerators, sulfenamide-based vulcanization accelerators, and guanidine-based vulcanization accelerators have been known, for example (Non Patent Literature 1).

CITATION LIST

Non Patent Literature

Non Patent Literature 1: Gomu Kogyo Binran (Rubber Industrial Handbook) <Fourth edition>, pp. 412 to 413, 1994, published by the Society of Rubber Science And Technology, Japan

SUMMARY OF INVENTION

Technical Problem

Rubber compositions containing conventional vulcanization aids do not have sufficient vulcanizing rates of rubber components.

Solution to Problem

The present invention includes the following inventions.
[1] A rubber composition comprising a compound having one or more groups represented by formula (X), and a rubber component:

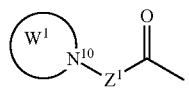
(X)

wherein ring $W^1$ represents a cyclic group having at least one selected from the group consisting of —C(=O)— and —C(=S)—; $N^{10}$ represents a nitrogen atom; the at least one selected from the group consisting of —C(=O)— and —C(=S)— in the ring $W^1$ and $N^{10}$ are conjugated; and $Z^1$ represents —O— or —S—.
[2] The rubber composition according to [1], wherein the ring $W^1$ is a 5-membered ring, a 6-membered ring, or a 7-membered ring.
[3] The rubber composition according to [1] or [2], wherein the ring $W^1$ is a cyclic group composed of $N^{10}$ and four, five, or six carbon atoms, one or more of the carbon atoms may be replaced with —O—, —NH—, —S—, or =N—, and the carbon atoms and —NH— may have a substituent.
[4] The rubber composition according to any one of [1] to [3], wherein the at least one selected from —C(=O)— and —C(=S)— is bonded to $N^{10}$.
[5] The rubber composition according to any one of [1] to [4], wherein the compound having one or more groups represented by the formula (X) is a compound having two or more groups represented by the formula (X).
[6] The rubber composition according to any one of [1] to [4], wherein the compound having one or more groups represented by the formula (X) is a compound represented by formula (I):

(I)

wherein $Y^1$ represents a group represented by the formula (X); $Y^2$ represents a hydrogen atom, a group represented by the formula (X), or a group represented by formula (b); and $R^2$ represents a divalent hydrocarbon group;

(b)

wherein $R^7$ and $R^8$ each independently represent a hydrogen atom, an alkyl group having 1 to 12 carbon atoms and optionally having a substituent, an aryl group having 6 to 20 carbon atoms and optionally having a substituent, or an aralkyl group having 7 to 18 carbon atoms and optionally having a substituent, or $R^7$ and $R^8$ are bonded to each other to form a ring together with a carbon atom bonded by $R^7$ and R.
[7] A rubber composition according to [6], wherein $Y^2$ is a group represented by the formula (X) or a group represented by the formula (b).
[8] The rubber composition according to [6], wherein $Y^2$ is a hydrogen atom, and $R^{20}$ is an alkanediyl group having 1 to 18 carbon atoms.
[9] The rubber composition according to any one of [1] to [4], wherein the compound having one or more groups represented by the formula (X) is a compound represented by formula (A1):

(A1)

wherein $Y^1$ represents a group represented by the formula (X); and $R^9$ represents an alkyl group having 1 to 12 carbon atoms and optionally having a substituent.
[10] The rubber composition according to any one of [1] to [9], further comprising a sulfur component.
[11] A vulcanized rubber obtained through a heat treatment of the rubber composition according to [10].

[12] A tire including a rubber member comprising a vulcanized rubber obtained through a heat treatment of the rubber composition according to [10] (tire obtainable through processing of the rubber composition).

[13] A vulcanization aid comprising a compound having one or more groups represented by formula (W) as an active component:

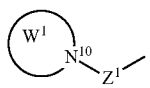
(W)

wherein ring $W^1$ has at least one selected from the group consisting of —C(=O)— and —C(=S)—; $N^{10}$ represents a nitrogen atom; the at least one selected from the group consisting of —C(=O)— and —C(=S)— in the ring $W^1$ and $N^{10}$ are conjugated; and $Z^1$ represents —O— or —S—.

[14] The vulcanization aid according to [13], wherein the ring $W^1$ is a 5-membered ring, a 6-membered ring, or a 7-membered ring.

[15] The vulcanizing aid according to [13] or [14], wherein the ring $W^1$ is a cyclic group composed of $N^{10}$ and four, five, or six carbon atoms, one or more of the carbon atoms may be replaced with —O—, —NH—, —S—, and =N—, and the carbon atoms and —NH— may have a substituent.

[16] The vulcanization aid according to any one of [13] to [15], wherein the at least one selected from —C(=O)— and —C(=S)— is bonded to $N^{10}$.

[17] The vulcanization aid according to any one of [13] to [16], wherein $Z^1$ is —O—.

[18] The vulcanization aid according to any one of [13] to [17], wherein the compound having one or more groups represented by the formula (W) is a compound having two or more groups represented by the formula (W).

[19] The vulcanization aid according to any one of [13] to [17], wherein the compound having one or more groups represented by the formula (W) is a compound represented by formula (II):

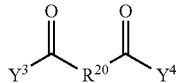
(II)

wherein $Y^3$ represents a group represented by the formula (W); $Y^4$ represents a hydrogen atom, a group represented by the formula (W), or a group represented by formula (c); and $R^{20}$ represents a divalent hydrocarbon group:

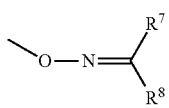
(c)

wherein $R^7$ and $R^8$ each independently represent a hydrogen atom, an alkyl group having 1 to 12 carbon atoms and optionally having a substituent, an aryl group having 6 to 20 carbon atoms and optionally having a substituent, or an aralkyl group having 7 to 18 carbon atoms and optionally having a substituent, or $R^7$ and $R^8$ are bonded to each other to form a ring together with a carbon atom bonded by $R^7$ and $R^8$.

[20] The vulcanization aid according to [19], wherein $Y^4$ is a group represented by the formula (W) or a group represented by the formula (c).

[21] The vulcanization aid according to any one of [13] to [17], wherein the compound having one or more groups represented by the formula (W) is a compound represented by formula (B):

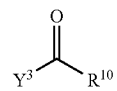
(B)

wherein $Y^3$ represents a group represented by the formula (W); and $R^{10}$ represents an alkyl group having 1 to 12 carbon atoms and optionally having a substituent.

[22] The vulcanization aid according to any one of [13] to [17], wherein the compound having one or more groups represented by the formula (W) is a compound represented by formula (A2):

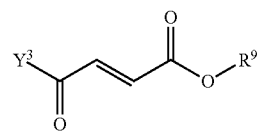
(A2)

wherein $Y^3$ represents a group represented by the formula (W); and $R^9$ represents an alkyl group having 1 to 12 carbon atoms and optionally having a substituent.

[23] A compound represented by formula (III):

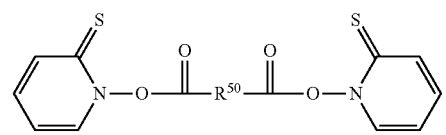
(III)

wherein $R^{50}$ represents an alkanediyl group having 5 to 9 carbon atoms.

Advantageous Effects of Invention

According to the rubber composition according to the present invention, the vulcanizing rate of the rubber component can be increased.

DESCRIPTION OF EMBODIMENTS

The rubber composition according to the present embodiment (hereinafter, referred to as the present rubber composition in some cases) comprises the compound having one or more groups represented by the above formula (X) (hereinafter, referred to as compound (X) in some cases) and a rubber component. The compound (X) is preferably the compound represented by the above formula (I) (hereinafter, referred to as compound (I) in some cases). The group represented by the formula (X) is a monovalent group in which the carbonyl carbon bonded to $Z^1$ is bonded to another group through a single bond.

The compound (X) may have two or more groups represented by the formula (X). As the compound (X), a compound having two groups represented by the formula (X) is preferred. Use of these compounds can provide a rubber composition having a particularly high vulcanizing rate and a particularly high reversion resistance.

The vulcanization aid according to the present embodiment comprises the compound having one or more groups represented by the above formula (W) (hereinafter, referred to as compound (W) in some cases) as an active component. The compound (W) is preferably the compound represented by the above formula (II) (hereinafter, referred to as compound (II) in some cases). The group represented by the formula (W) is a monovalent group in which $Z^1$ is bonded to another group through a single bond.

The compound (W) may have one or more groups represented by the formula (W); a compound having two groups represented by the formula (W) is preferred. Thereby, a particularly high vulcanizing rate and particularly high reversion resistance can be obtained.

The vulcanization aid promotes the action of the vulcanizing agent in the rubber composition. In other words, the vulcanization aid is a component which enhances the vulcanizing rate of the rubber composition when the aid is added to the rubber composition.

The vulcanization aid having two or more groups represented by the formula (W) is preferred because the vulcanization aid can be used as a vulcanization accelerator to enhance the vulcanizing rate of the rubber component, as well as an anti-reversion agent to provide a rubber composition having high reversion resistance.

The ring $W^1$ has at least one selected from the group consisting of —C(=O)— and —C(=S)—, preferably —C(=S)—. The at least one selected from the group consisting of —C(O)— and —C(=S)— in the ring $W^1$ and $N^{10}$ are conjugated, and are preferably bonded.

In this specification, the phrase "the at least one selected from the group consisting of —C(=O)— and —C(=S)— and $N^{10}$ are conjugated" indicates a state where electrons are delocalized in the p orbital of the at least one selected from the group consisting of —C(=O)— and —C(=S)— and the p orbital of $N^{10}$.

The ring $W^1$ is preferably a 5-membered ring, a 6-membered ring, or a 7-membered ring.

The ring $W^1$ is preferably a cyclic group composed of $N^{10}$ and four, five, or six carbon atoms. The carbon atoms may be replaced with —O—, —NH—, —S—, or =N—. Preferably two or less of the carbon atoms, more preferably one or less of the carbon atoms may be replaced with —O—, —NH—, —S—, or =N—. It is more preferred that all of the carbon atoms which form the cyclic group with $N^{10}$ be not replaced with —O—, —NH—, —S—, or =N—.

The carbon atoms are usually bonded to hydrogen atoms. The carbon atoms and —NH— may have a substituent (for example, hydrogen bonded to nitrogen may be replaced with a substituent). The ring $W^1$ may be a cyclic group not having a substituent other than the group bonded to $N^{10}$. At least one of the carbon atoms is bonded to an oxygen atom or a sulfur atom to form —C(=O)— or —C(=S)—.

Examples of the substituent include halogen atoms, alkyl groups having 1 to 12 carbon atoms and optionally having a substituent, aryl groups having 6 to 20 carbon atoms and optionally having a substituent, a nitro group, a cyano group, and substituents in which a nitro group and a cyano group are bonded to each other to form a ring together with a carbon atom or a nitrogen atom bonded by these groups.

Examples of the alkyl groups having 1 to 12 carbon atoms and optionally having a substituent include linear or branched alkyl groups such as a methyl group, an ethyl group, a propyl group, an isopropyl group, a butyl group, an isobutyl group, a sec-butyl group, a tert-butyl group, a pentyl group, and a hexyl group; cyclic alkyl groups such as a cyclopropyl group, a 2,2-dimethylcyclopropyl group, a cyclopentyl group, and a cyclohexyl group; alkyl groups having halogen atoms such as a chloromethyl group, a fluoromethyl group, and a trifluoromethyl group; alkyl groups having alkoxy groups such as a methoxymethyl group, an ethoxymethyl group, a 1-methoxyethyl group, and a 2-methoxyethyl group; alkyl groups having alkoxycarbonyl groups such as a methoxycarbonylmethyl group and a 1-ethoxycarbonyl-2,2-dimethyl-3-cyclopropyl group; alkyl groups having aryl groups such as a phenylmethyl group and a phenylethyl group; alkyl groups having heteroaryl groups such as a 2-pyridylmethyl group and a 3-pyridylmethyl group; and alkyl groups having alkylthio groups such as a 2-methylthioethyl group.

Examples of the aryl groups having 6 to 20 carbon atoms and optionally having a substituent include a phenyl group, a 2-methylphenyl group, a 4-methylphenyl group, a 4-chlorophenyl group, a 4-methoxyphenyl group, a 3-phenoxyphenyl group, a 1-naphthyl group, and a 2-naphthyl group.

Specific examples of the group represented by the formula (X) are listed below:

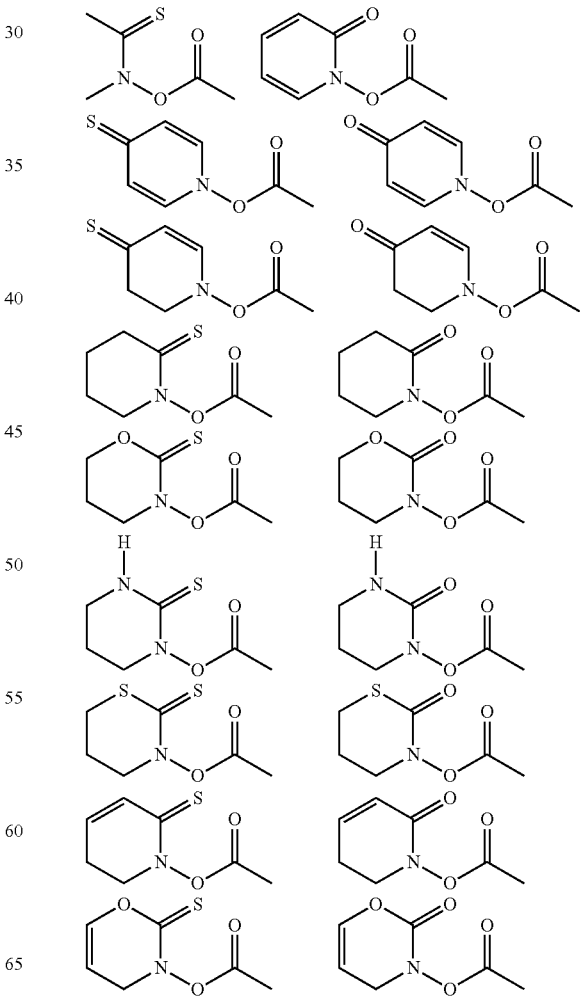

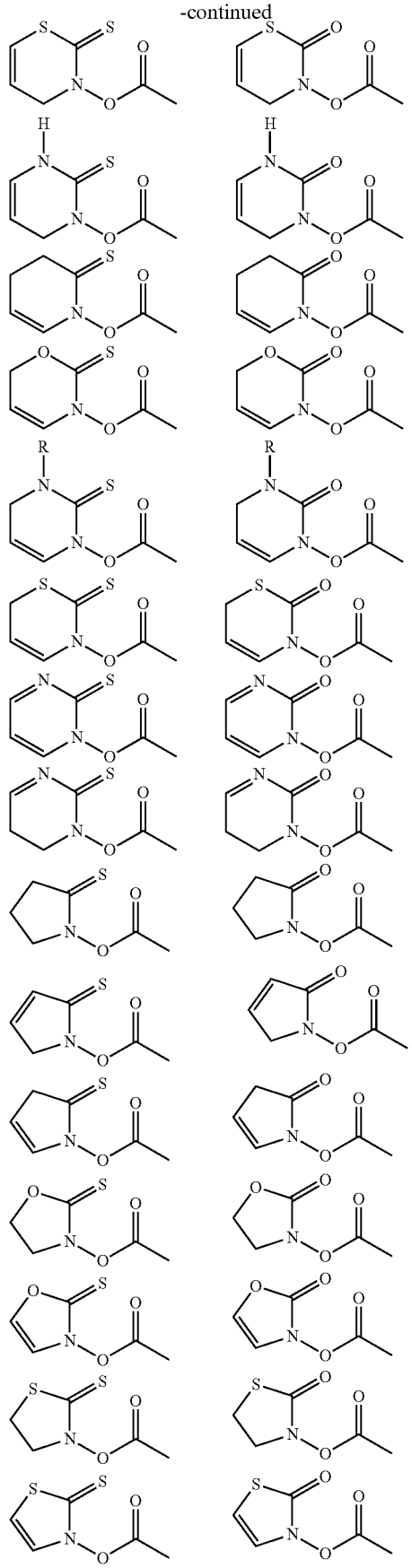
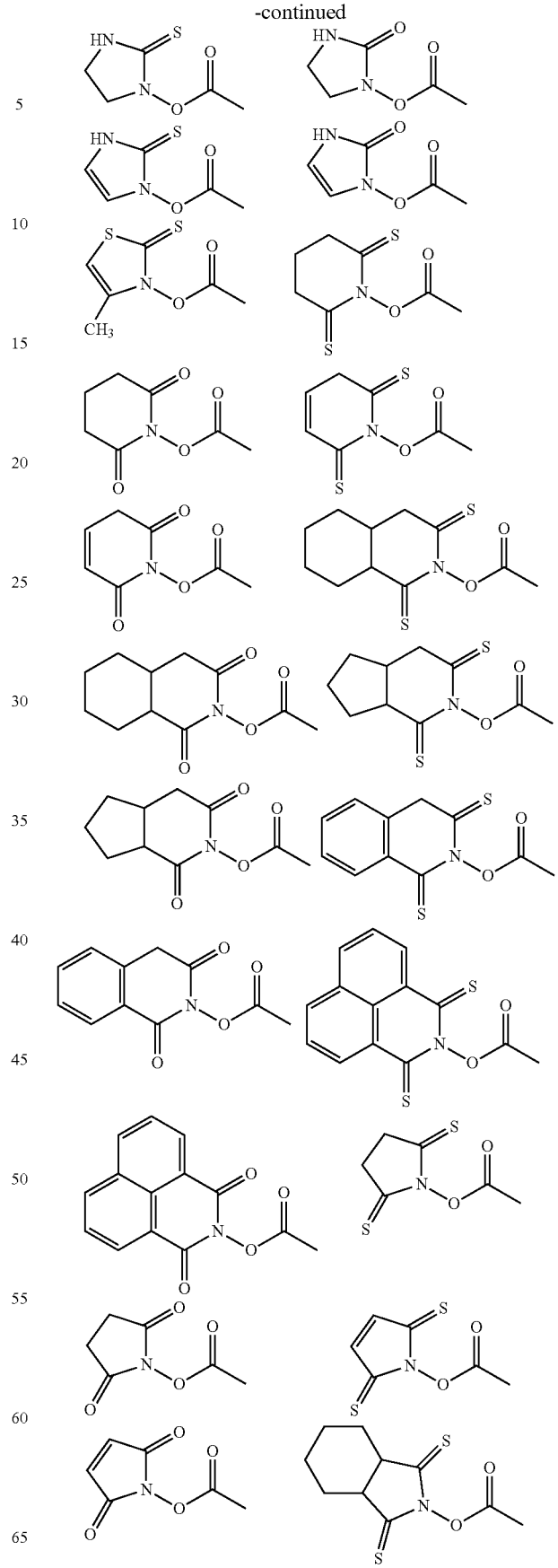

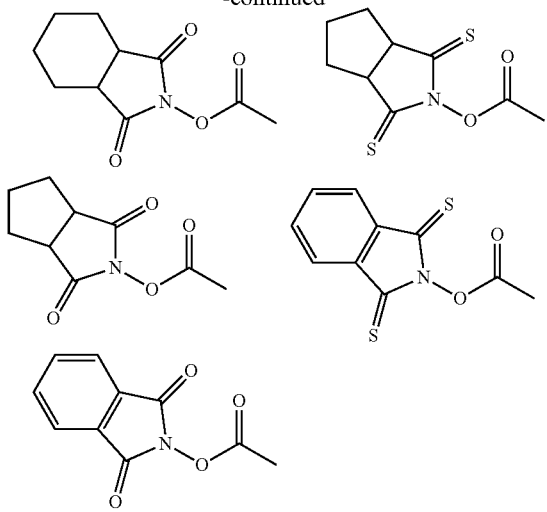
Specific examples of the group represented by the formula (W) are listed below:
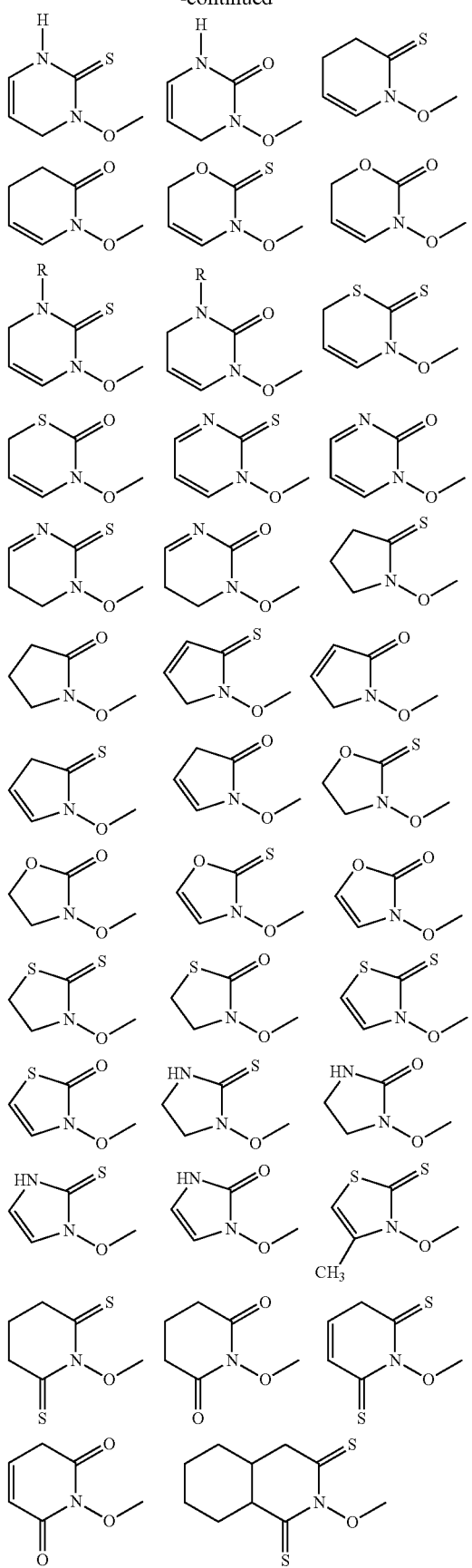

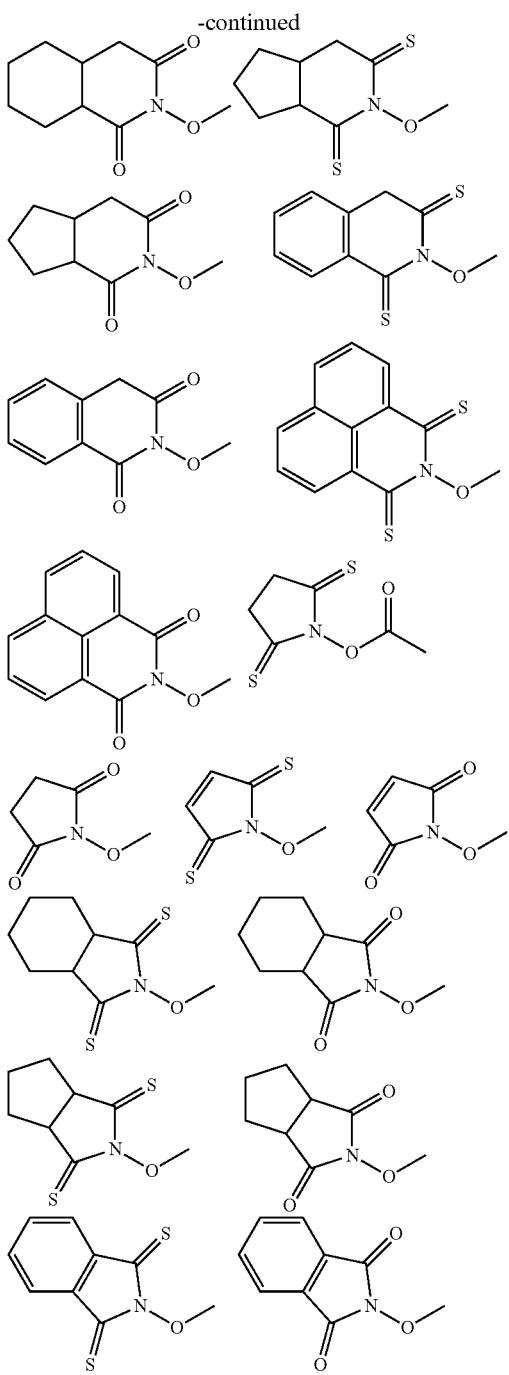

The compound (X) may be a compound represented by the formula (I) (hereinafter, referred to as compound (I) in some cases). In the formula (I), $Y^2$ is preferably a group represented by the formula (X) or a group represented by the formula (b), more preferably a group represented by the formula (X).

From the viewpoint of the reversion resistance, a compound (I) in which $Y^2$ is a group represented by the formula (X) or a group represented by the formula (b) is useful, and a rubber composition comprising such a compound (I) has high reversion resistance. From the same viewpoint, a compound (I) in which $Y^2$ is a hydrogen atom and $R^{20}$ is an alkanediyl group having 1 to 18 carbon atoms, and a compound represented by the formula (A1) (hereinafter, referred to as compound A1 in some cases) are also useful.

$Y^4$ is preferably a group represented by the formula (W) or a group represented by the formula (c), more preferably a group represented by the formula (W).

From the viewpoint of the reversion resistance, a compound (II) in which $Y^4$ is a group represented by the formula (W) or a group represented by the formula (c) is useful, and a rubber composition comprising such a compound (11) has high reversion resistance. From the same viewpoint, a compound represented by the formula (B) (hereinafter, referred to as compound (B) in some cases), and a compound represented by the formula (A2) (hereinafter, referred to as compound (A2) in some cases) are also useful. The compound (B) corresponds to the compound (I) in which $Y^2$ is a hydrogen atom and $R^{20}$ is an alkanediyl group having 1 to 18 carbon atoms. The compound (A2) corresponds to the compound (A1).

In the compound (I), $Y^1$ and $Y^2$ are preferably the same.

In the compound (II), $Y^3$ and $Y^4$ are preferably the same.

Examples of the alkyl groups having 1 to 12 carbon atoms and optionally having a substituent, which are represented by $R^7$ or Re in the formulae (b) and (c) include linear or branched alkyl groups such as a methyl group, an ethyl group, a propyl group, an isopropyl group, a butyl group, an isobutyl group, a sec-butyl group, a tert-butyl group, a pentyl group, and a hexyl group; cyclic alkyl groups such as a cyclopropyl group, a 2,2-dimethylcyclopropyl group, a cyclopentyl group, and a cyclohexyl group; alkyl groups having halogen atoms such as a chloromethyl group, a fluoromethyl group, and a trifluoromethyl group; alkyl groups having alkoxy groups such as a methoxymethyl group, an ethoxymethyl group, a 1-methoxyethyl group, and a 2-methoxyethyl group; alkyl groups having alkoxycarbonyl groups such as a methoxycarbonylmethyl group and a 1-ethoxycarbonyl-2,2-dimethyl-3-cyclopropyl group; alkyl groups having aryl groups such as a phenylmethyl group and a phenylethyl group; alkyl groups having heteroaryl groups such as a 2-pyridylmethyl group and a 3-pyridylmethyl group; and alkyl groups having alkylthio groups such as a 2-methylthioethyl group.

Examples of the aryl groups having 6 to 20 carbon atoms and optionally having a substituent include a phenyl group, a 2-methylphenyl group, a 4-methylphenyl group, a 4-chlorophenyl group, 4-methoxyphenyl group, a 3-phenoxyphenyl group, a 1-naphthyl group, and a 2-naphthyl group.

Examples of the aralkyl groups having 7 to 18 carbon atoms and optionally having a substituent include a phenylmethyl group and a phenylethyl group.

$R^7$ is preferably a hydrogen atom, an alkyl group having 1 to 6 carbon atoms, an aryl group having 6 to 12 carbon atoms, or an aralkyl group having 7 to 18 carbon atoms, more preferably an alkyl group having 1 to 6 carbon atoms, still more preferably a methyl group.

$R^8$ is preferably a hydrogen atom, an alkyl group having 1 to 6 carbon atoms, an aryl group having 6 to 12 carbon atoms, or an aralkyl group having 7 to 18 carbon atoms, more preferably an aryl group having 6 to 12 carbon atoms, still more preferably a phenyl group.

Specific examples of the group represented by the formula (b) are listed below:

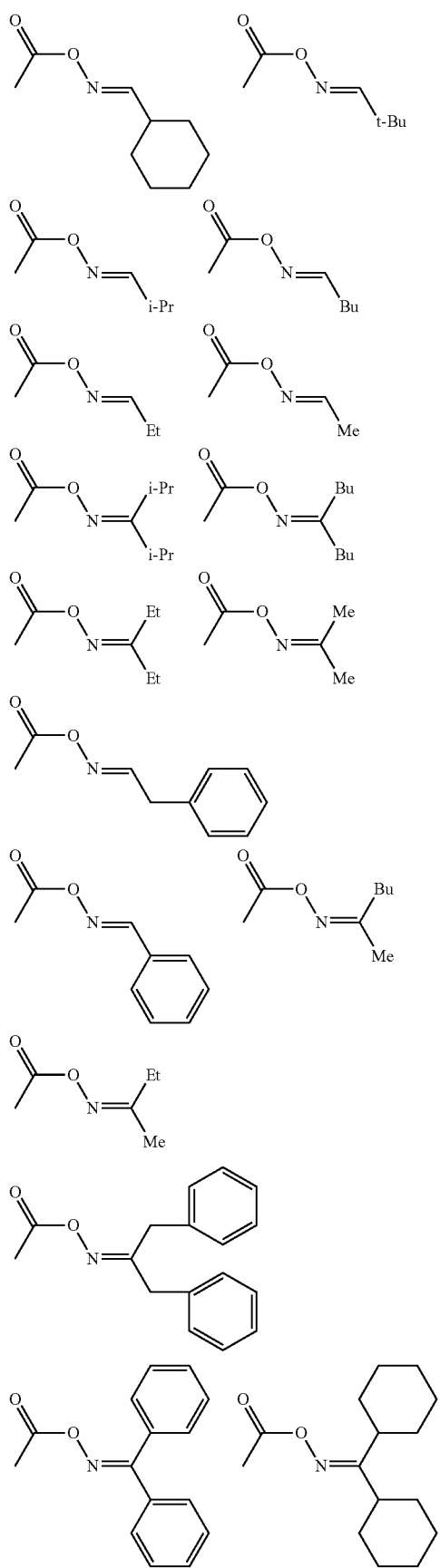
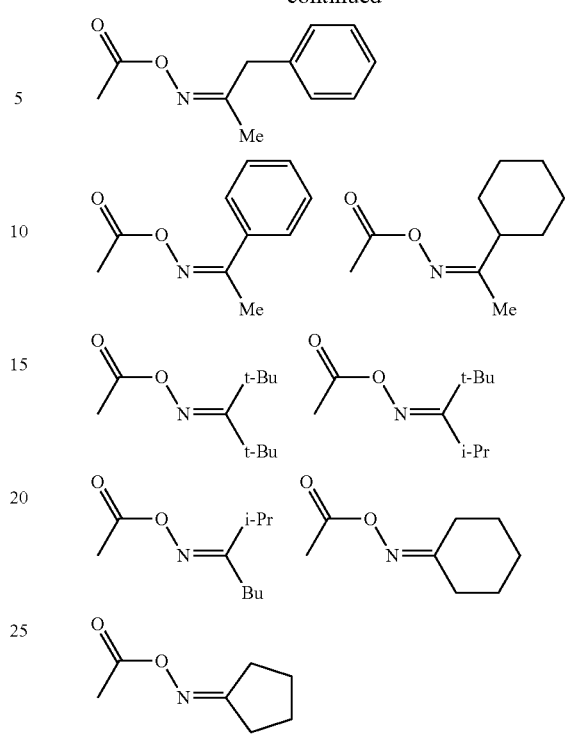
Specific examples of the group represented by the formula (c) are listed below:
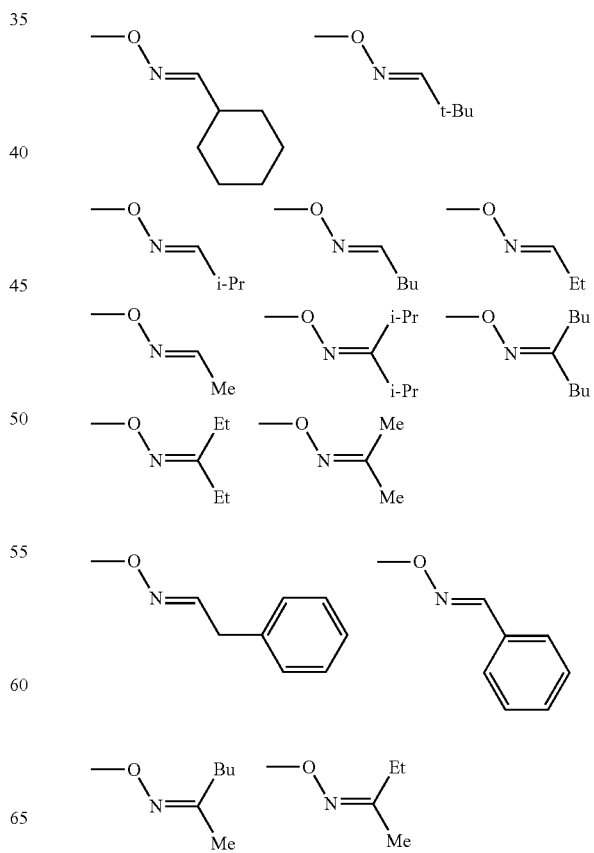

-continued

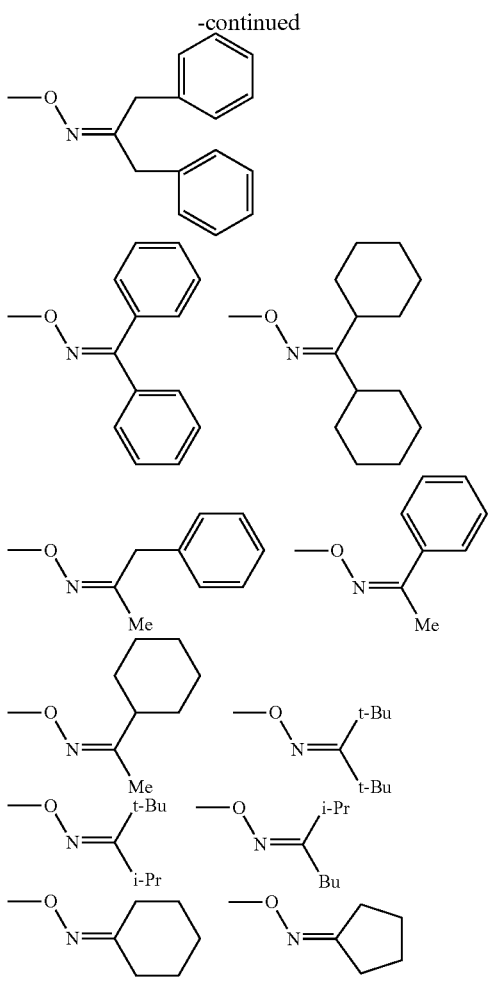

Examples of the divalent hydrocarbon group represented by $R^{20}$ in the formula (I) include alkanediyl groups having 1 to 18 carbon atoms, cycloalkanediyl groups having 3 to 12 carbon atoms, arylene groups having 6 to 12 carbon atoms, aralkylene groups having 7 to 15 carbon atoms, alkarylene groups having 8 to 18 carbon atoms, and groups composed of combinations thereof; the divalent hydrocarbon group represented by $R^{20}$ in the formula (I) is preferably an alkanediyl group having 1 to 18 carbon atoms or an arylene group having 6 to 12 carbon atoms, more preferably an alkanediyl group having 1 to 18 carbon atoms, still more preferably an alkanediyl group having 5 to 9 carbon atoms.

Examples of the alkanediyl groups having 1 to 18 carbon atoms include linear alkanediyl groups such as a methylene group, an ethylene group, a trimethylene group, a tetramethylene group, a pentamethylene group, a hexamethylene group, an octamethylene group, a decamethylene group, and a dodecamethylene group; and branched alkanediyl groups such as a propylene group, an isopropylene group, an isobutylene group, a 2-methyltrimethylene group, an isopentylene group, an isohexylene group, an isooctylene group, a 2-ethylhexylene group, and an isodecylene group.

Examples of the cycloalkanediyl groups having 3 to 12 carbon atoms include a cyclopropylene group, a cyclopentylene group, a cyclohexylene group, and a cyclododecylene group.

Examples of the arylene groups having 6 to 12 carbon atoms include a 1,2-phenyl group, a 1,3-phenyl group, a 1,4-phenyl group, a biphenyl-4,4'-diyl group, a biphenylmethane-4,4'-diyl group, and a 3,3'-dimethylbiphenylmethane-4,4'-diyl group.

Examples of the aralkylene groups having 7 to 15 carbon atoms include a phenylethylene group, a phenylmethylene group, and a phenylpropylene group.

Examples of the alkarylene groups having 8 to 18 carbon atoms include an o-xylylene group, an m-xylylene group, and a p-xylylene group.

Examples of the alkyl groups having 1 to 12 carbon atoms and optionally having a substituent, which are represented by $R^9$ in the formulae (A1) and (A2), include linear or branched alkyl groups such as a methyl group, an ethyl group, a propyl group, an isopropyl group, a butyl group, an isobutyl group, a sec-butyl group, a tert-butyl group, a pentyl group, and a hexyl group; cyclic alkyl groups such as a cyclopropyl group, a 2,2-dimethylcyclopropyl group, a cyclopentyl group, and a cyclohexyl group; alkyl groups having halogen atoms such as a chloromethyl group, a fluoromethyl group, and a trifluoromethyl group; alkyl groups having alkoxy groups such as a methoxymethyl group, an ethoxymethyl group, a 1-methoxyethyl group, and a 2-methoxyethyl group; alkyl groups having alkoxycarbonyl groups such as a methoxycarbonylmethyl group and a 1-ethoxycarbonyl-2,2-dimethyl-3-cyclopropyl group; alkyl groups having aryl groups such as a phenylmethyl group and a phenylethyl group; alkyl groups having heteroaryl groups such as a 2-pyridylmethyl group and a 3-pyridylmethyl group; and alkyl groups having alkylthio groups such as a 2-methylthioethyl group.

$R^9$ is preferably an alkyl group having 1 to 8 carbon atoms, more preferably an ethyl group.

Examples of the alkyl groups having 1 to 12 carbon atoms and optionally having a substituent, which are represented by $R^{10}$ in the formula (B), include linear or branched alkyl groups such as a methyl group, an ethyl group, a propyl group, an isopropyl group, a butyl group, an isobutyl group, a sec-butyl group, a tert-butyl group, a pentyl group, and a hexyl group; cyclic alkyl groups such as a cyclopropyl group, a 2,2-dimethylcyclopropyl group, a cyclopentyl group, and a cyclohexyl group; alkyl groups having halogen atoms such as a chloromethyl group, a fluoromethyl group, and a trifluoromethyl group; alkyl groups having alkoxy groups such as a methoxymethyl group, an ethoxymethyl group, a 1-methoxyethyl group, and a 2-methoxyethyl group; alkyl groups having alkoxycarbonyl groups such as a methoxycarbonylmethyl group and a 1-ethoxycarbonyl-2,2-dimethyl-3-cyclopropyl group; alkyl groups having aryl groups such as a phenylmethyl group and a phenylethyl group; alkyl groups having heteroaryl groups such as a 2-pyridylmethyl group and a 3-pyridylmethyl group; and alkyl groups having alkylthio groups such as a 2-methylthioethyl group.

$R^{10}$ is preferably an alkyl group having 1 to 10 carbon atoms.

Examples of the alkanediyl group having 5 to 9 carbon atoms, which are represented by $R^{50}$ in the formula (I), include linear alkanediyl groups such as a pentamethylene group, a hexamethylene group, an octamethylene group, and a nonamethylene group; and branched alkanediyl groups such as a propylene group, an isohexylene group, an isooctylene group, and a 2-ethylhexylene group. Among these, alkanediyl groups having 5 to 7 carbon atoms are more preferred as $R^{50}$.

In the formulae (X) and (W), $Z^1$ is preferably —O—.

Examples of the compound (W) other than the compound (II) include a compound represented by a formula (W1) and a compound represented by a formula (W2):

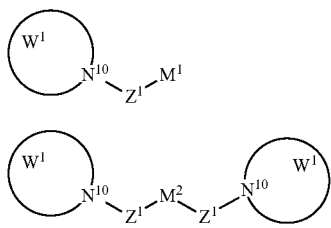

wherein $M^1$ represents a hydrogen atom or a monovalent metal atom; and $M^2$ represents a divalent metal atom.

Examples of the monovalent metal atom represented by $M^1$ include lithium, sodium, potassium, and copper; the monovalent metal atom is preferably sodium and potassium.

Examples of the divalent metal atom represented by $M^2$ include magnesium, calcium, aluminum, manganese, iron, cobalt, nickel, copper, and zinc; the divalent metal atom is preferably zinc.

Specific examples of the compound (X) are listed below:

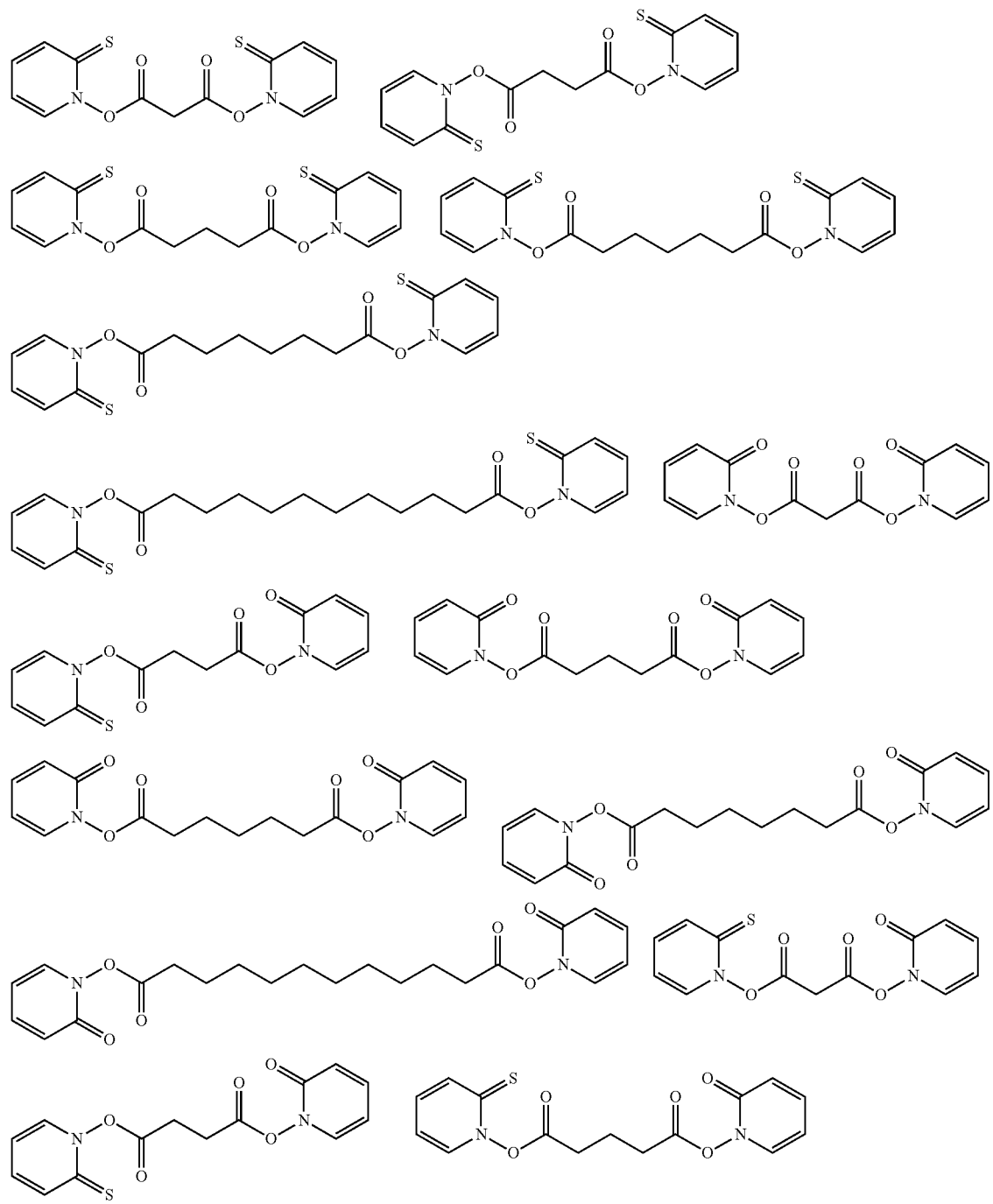

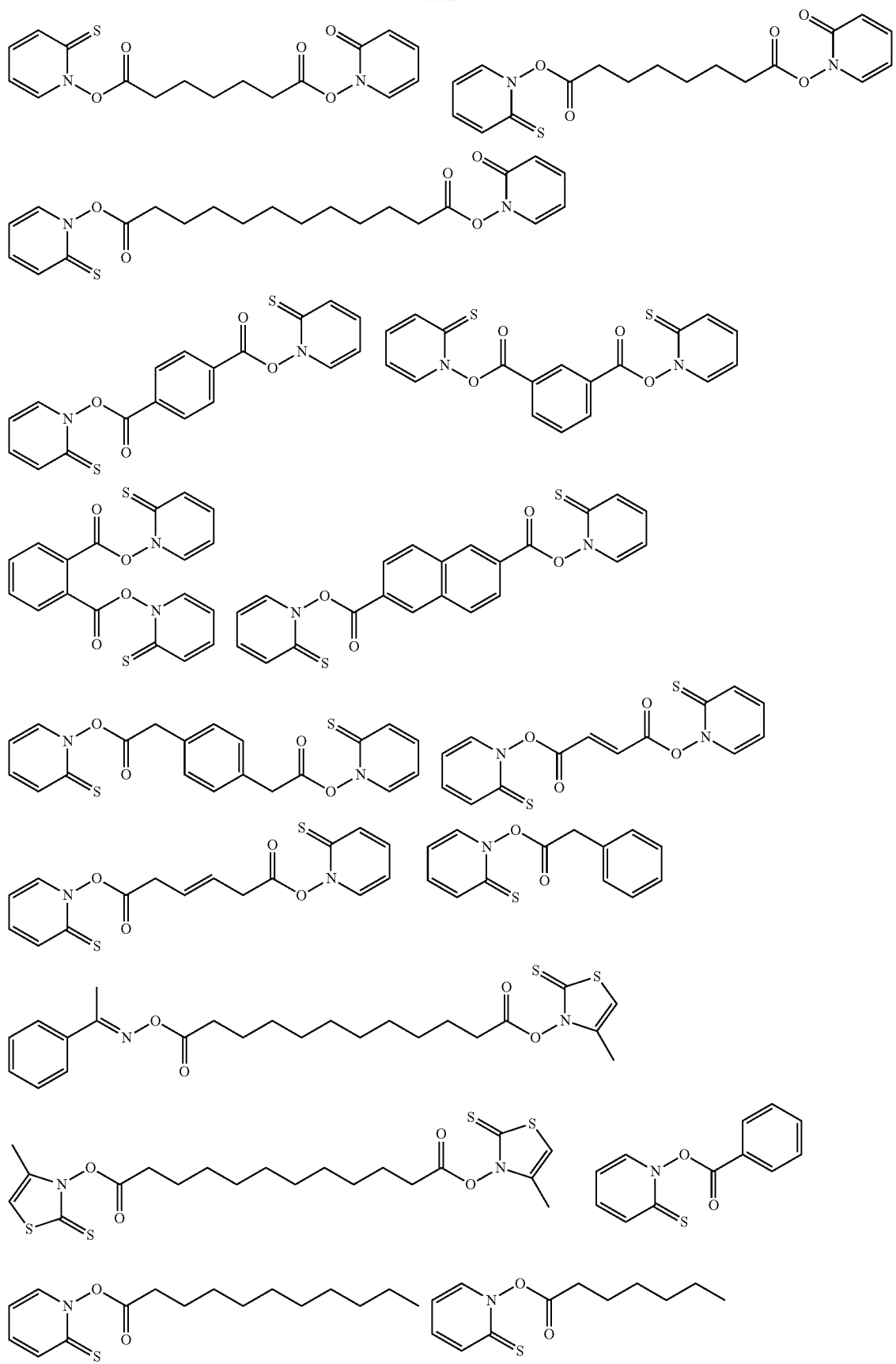

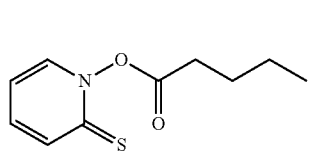
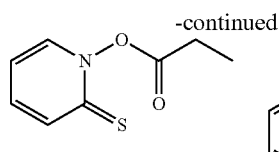
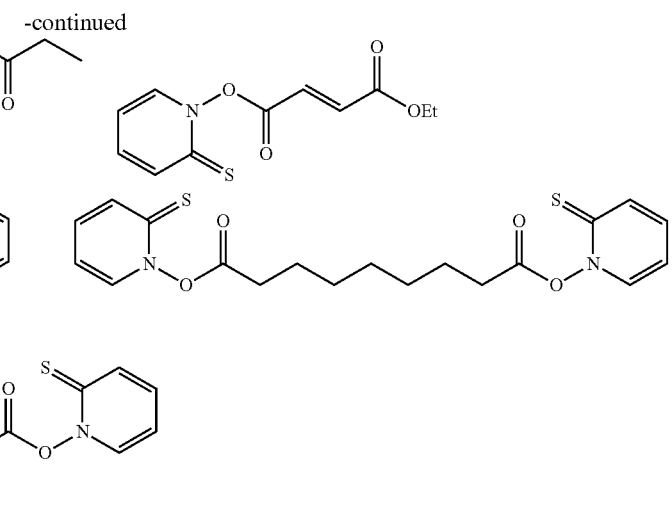
Specific examples of the compound (W) are listed below:
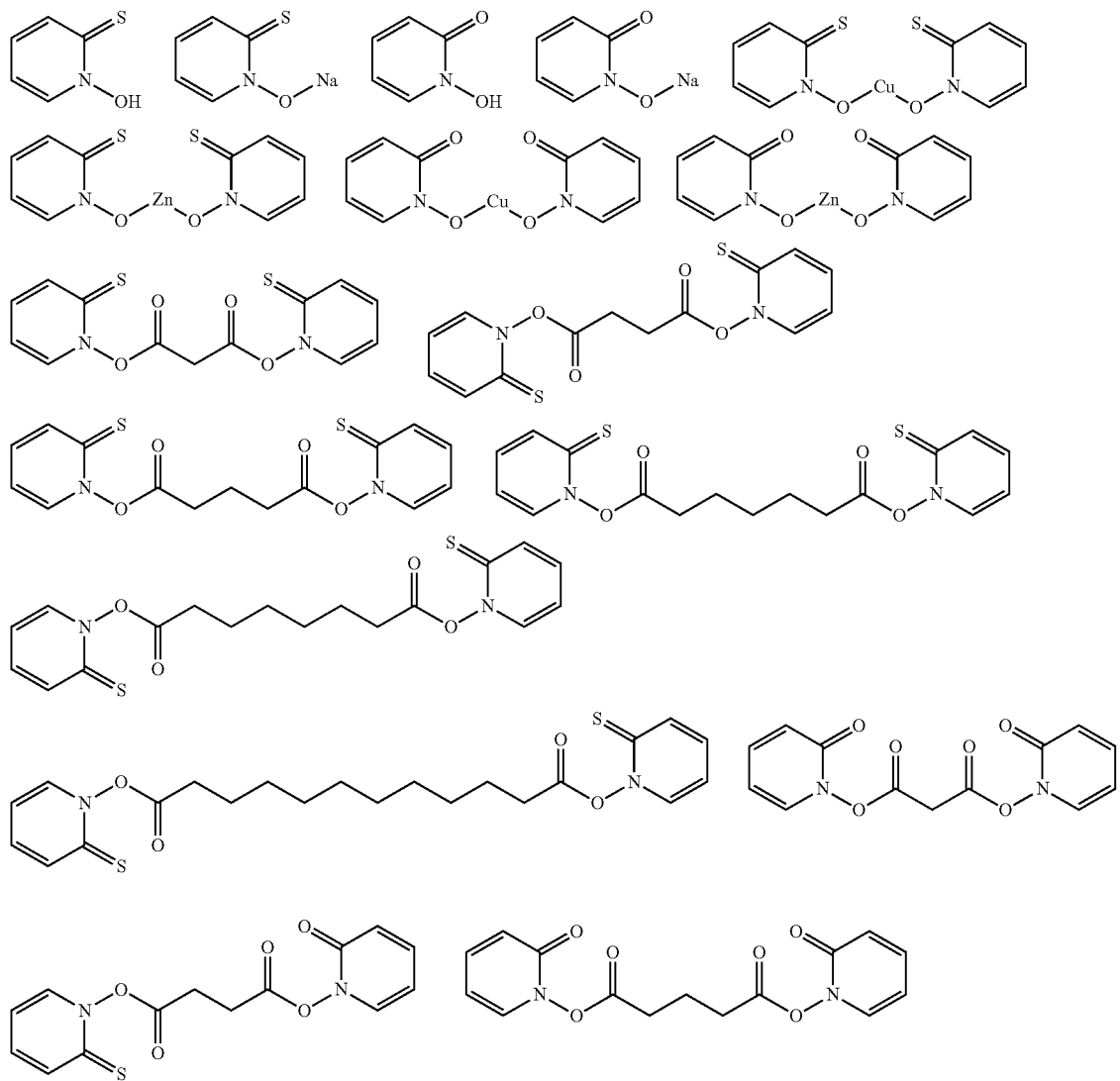

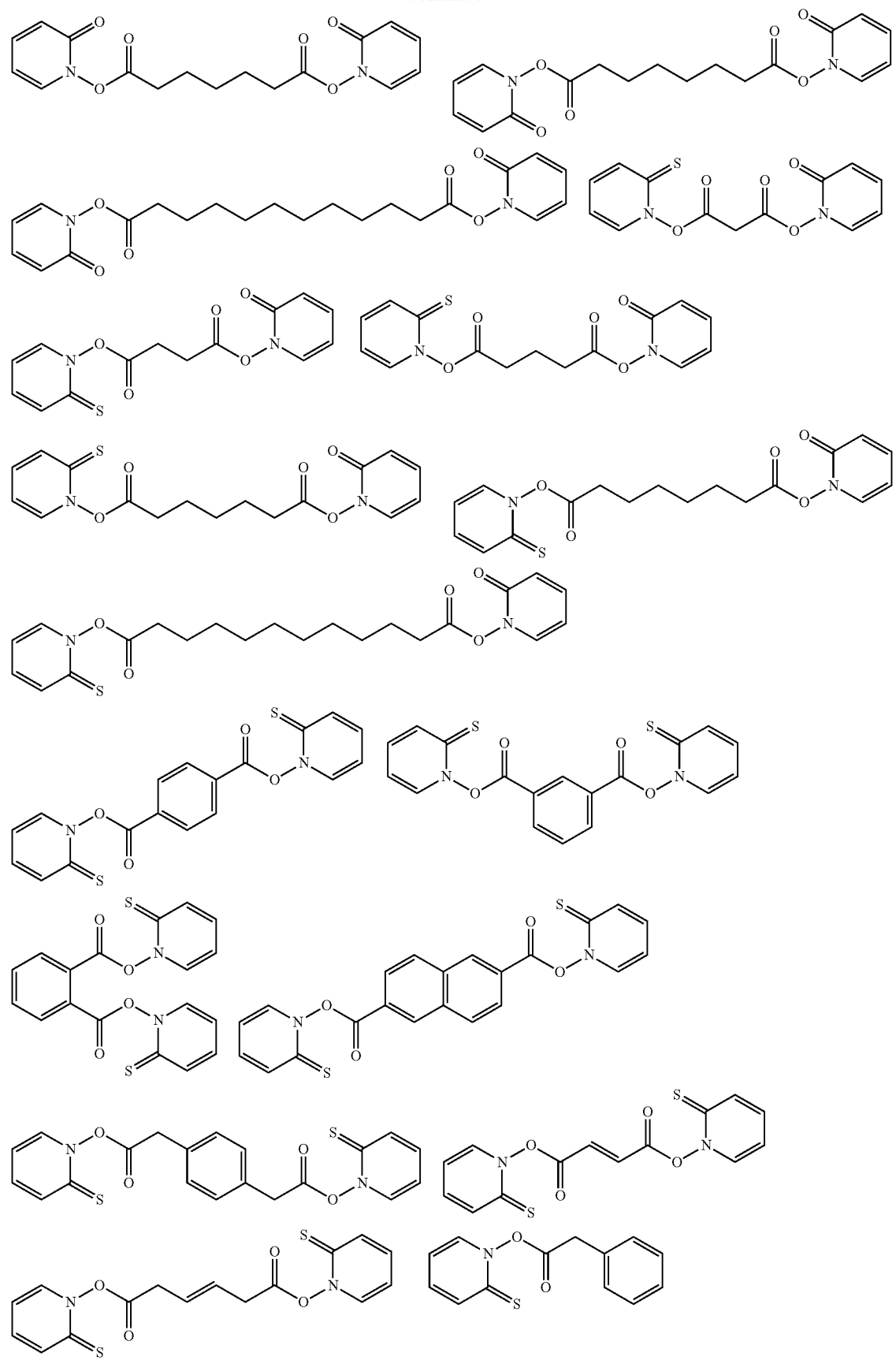

-continued

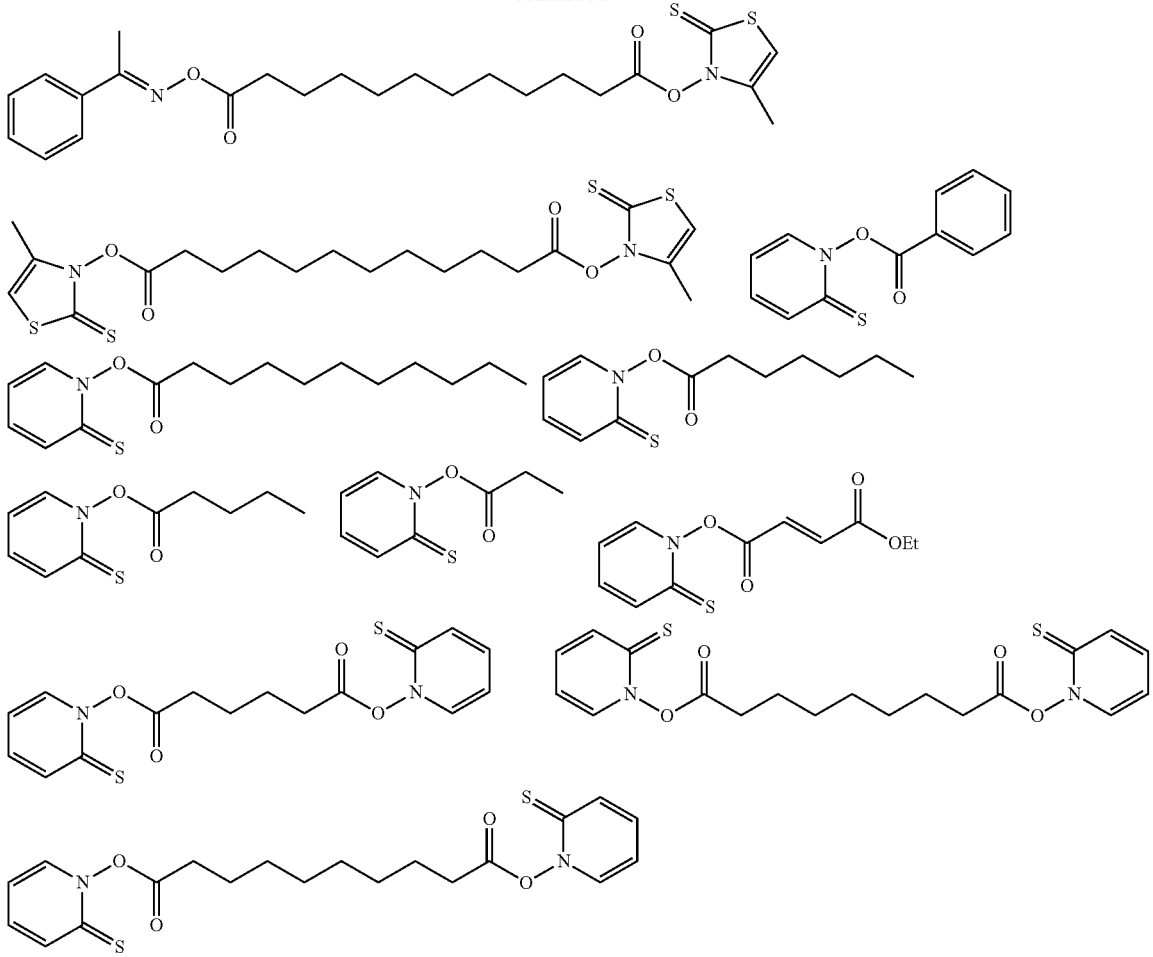

Examples of commercially available products of the compound (W) include 2-mercaptopyridine N-oxide (Tokyo Chemical Industry Co., Ltd.), 2-hydroxypyridine N-oxide (Tokyo Chemical Industry Co., Ltd.), 2-mercaptopyridine N-oxide sodium (Tokyo Chemical Industry Co., Ltd.), 2-mercaptopyridine N-oxide zinc (Tokyo Chemical Industry Co., Ltd.), and 2-mercaptopyridine N-oxide copper (Wako Pure Chemical Industries, Ltd.).

The compounds (X) and (W) can be produced by the method shown in the following scheme, for example.

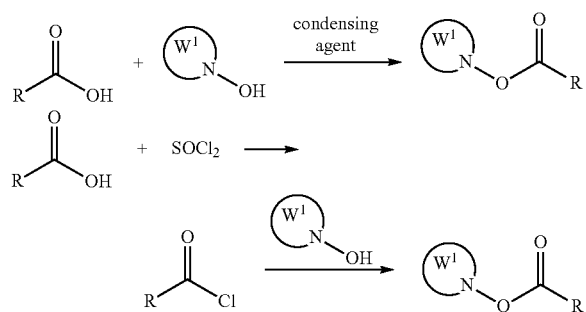

wherein R represents an organic group; and $W^1$ represents the same meaning as above.

It is preferred that the reaction between carboxylic acid and hydroxylamine in the presence of a condensing agent be performed in the presence of a solvent; examples of the solvent include halogen-based solvents such as chloroform. After the reaction, a typical refining operation can be performed to obtain a compound (X) or (W). As the condensing agent, a reagent usually used in the esterification reaction of carbodiimide or the like is used.

The reaction between carboxylic acid and thionyl chloride may be performed in the presence of a solvent or in the absence of a solvent. Examples of the solvent include apolar solvents such as toluene. After the reaction, a typical refining operation can be performed to obtain carboxylic chloride. The subsequent reaction between hydroxylamine and carboxylic chloride is performed in the presence of a base such as pyridine. After the reaction, a typical refining operation can be performed to obtain a compound (X) or (W).

The compounds (I) and (II) can be produced by the method shown in the following scheme, for example. The compound represented by the formula (III) can be also produced by the same method.

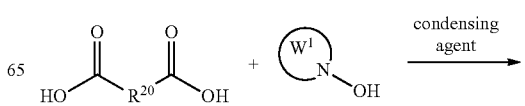

-continued wherein $W^1$ and $R^{20}$ represent the same meaning as above.

Examples of the reaction conditions include the same conditions as those in production of the compound (X) or (W).

The reaction between metal hydroxide (MOH) and hydroxylamine is usually performed in the presence of a solvent. Examples of the solvent include protic polar solvents such as water. After the reaction, a typical refining operation can be performed to obtain a compound (W).

The reaction between a metal salt and N-oxide sodium is usually performed in the presence of a solvent. Examples of the solvent include protic polar solvents such as water. After the reaction, a typical refining operation can be performed to obtain a compound (W). Examples of the metal salt include metal salts of sulfonic acid, metal salts of nitric acid, and metal oxides.

The compounds (A1) and (A2) can be produced by the method shown in the following scheme, for example.

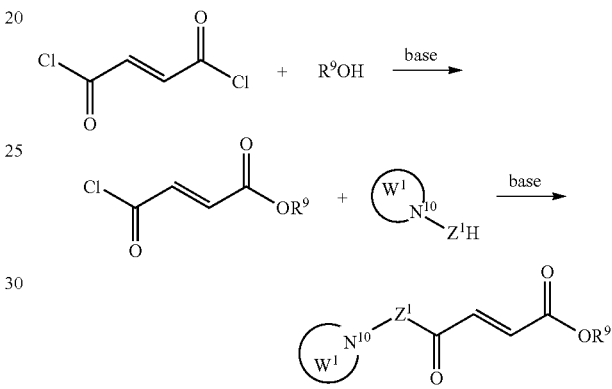

wherein $R^9$, $W^1$, $N^{10}$, and $Z^1$ represent the same meaning as above.

The reaction between fumaric dichloride and alcohol is usually performed in an apolar solvent such as chloroform in the presence of a base such as pyridine. After the reaction, the reaction with hydroxylamines is performed without performing a refining operation. The reaction is usually performed in an apolar solvent such as chloroform in the presence of a base such as pyridine. After the reaction, a typical refining operation can be performed to obtain compounds (A1) and (A2).

The compound (W) is contained in the rubber component to function as a vulcanization aid similarly to the compound (X). In the following description, the compound (X) can be replaced with the compound (W), and the present rubber composition can be replaced with a rubber composition comprising the compound (W) and the rubber component.

It is preferred that the present rubber composition be a rubber composition obtainable through kneading of the compound (X) and the rubber component. It is preferred that the present rubber composition further contain a filler and a sulfur component, and it is more preferred that the present rubber composition further contain a vulcanization accelerator different from the compound (X) and zinc oxide.

The rubber component may be, for example, at least one selected from the group consisting of natural rubber, modified natural rubber (such as epoxidized natural rubber, deproteinized natural rubber), polyisoprene rubber (IR), styrene-butadiene copolymerized rubber (SBR), polybutadiene rubber (BR), acrylonitrile-butadiene copolymerized rubber (NBR), isoprene-isobutylene copolymerized rubber (IIR), ethylene-propylene-diene copolymerized rubber (EPDM), and halogenated butyl rubber (HR). The rubber component is preferably highly unsaturated rubber such as natural rubber, styrene-butadiene copolymerized rubber, and polybutadiene rubber, and is particularly preferably natural rubber. A combination of several rubber components, such as a combination of natural rubber and styrene-butadiene copolymerized rubber, or a combination of natural rubber and polybutadiene rubber may be used.

Examples of the natural rubber can include natural rubbers of RSS#1, RSS#3, TSR20, and SIR20 grades. As the epoxidized natural rubber, those having a degree of epoxidation of 10 to 60 mol % are preferred; examples thereof include ENR25 and ENR50 manufactured by Kumpulan Guthrie Berhad. As the deproteinized natural rubber, a deproteinized natural rubber having a total nitrogen content of 0.3% by weight or less is preferred. Examples of the modified natural rubber include modified natural rubbers having polar groups and obtained through a preliminary reaction of natural rubber and 4-vinylpyridine, N,N,-dialkylaminoethyl acrylate (such as N,N,-diethylaminoethyl acrylate), or 2-hydroxy acrylate.

Examples of SBR include emulsion polymerized SBR and solution polymerized SBR described in "Gomu Kogyo Binran (Rubber Industrial Handbook) <Fourth edition>," pp. 210 to 211, edited by the Society of Rubber Science And Technology, Japan. Among these, the solution polymerized SBR is preferred as a rubber composition for a tread.

Examples of the solution polymerized SBR include solution polymerized SBRs obtained through modification of the molecular terminals with lactam compounds, amide compounds, urea-based compounds, N,N-dialkylacrylamide compounds, isocyanate compounds, imide compounds, silane compounds having an alkoxy group such as trialkoxysilane compounds, aminosilane compounds, tin compounds and silane compounds having an alkoxy group, and/or alkylacrylamide compounds and silane compounds having an alkoxy group, and thus having, at the molecular terminals, at least one element selected from the group consisting of nitrogen, tin and silicon.

Examples of the solution polymerized SBR specifically include solution polymerized SBRs whose molecular terminals are modified with 4,4'-bis-(dialkylamino)benzophenone such as "Nipol (registered trademark) NS116" manufactured by ZEON Corporation, solution polymerized SBRs whose molecular terminals are modified with a halogenated tin compound, such as "SL574" manufactured by JSR Corporation, and silane-modified solution polymerized SBRs such as "E10" and "E15" manufactured by Asahi Kasei Corporation.

Moreover, oil extended SBRs prepared through addition of oils such as process oil or aroma oil to emulsion polymerized SBRs and solution polymerized SBRs after polymerization are also preferred as the rubber composition for a tread.

Examples of BRs include solution polymerized BRs such as high-cis BR having a cis-1,4 bond of 90% or more and low-cis BR having a cis bond of around 35%; among these, high-cis BR having a high vinyl content is preferred.

Examples of the solution polymerized BR include solution polymerized BRs obtained through modification of the molecular terminals with 4,4'-bis-(dialkylamino)benzophenone, halogenated tin compounds, lactam compounds, amide compounds, urea-based compounds, N,N-dialkylacrylamide compounds, isocyanate compounds, imide compounds, silane compounds having an alkoxy group such as trialkoxysilane compounds, aminosilane compound, tin compounds and silane compounds having an alkoxy group, and/or alkylacrylamide compounds and silane compounds having an alkoxy group, and having, at the molecular terminals, at least one element selected from the group consisting of nitrogen, tin and silicon.

Examples of BRs specifically include tin-modified BRs such as "Nipol (registered trademark) BR 1250H" manufactured by ZEON Corporation.

These BRs are preferably usually mixed with SBR and/or natural rubber and used as a rubber composition for a tread and a rubber composition for a side wall. In the mixing proportion, it is preferred in the rubber composition for a tread that the content of SBR and/or natural rubber be 60 to 100% by weight and that the content of BR be 0 to 40% by weight based on the total rubber weight; it is preferred in the rubber composition for a side wall that the content of SBR and/or natural rubber be 10 to 70% by weight and that the content of BR be 90 to 30% by weight based on the total rubber weight; and further, a blend containing 40 to 60% by weight of natural rubber and 60 to 40% by weight of BR based on the total rubber weight is particularly preferred. In this case, a blend of modified SBR and non-modified SBR or a blend of modified BR and non-modified BR is also preferred.

Examples of the filler include carbon black, silica, talc, clay, aluminum hydroxide, and titanium oxide, which are usually used in the technical field of rubber; carbon black and silica are preferred, and carbon black is more preferred. Examples of carbon black include those described in "Gomu Kogyo Binran (Rubber Industrial Handbook) <Fourth edition>," p. 494, edited by the Society of Rubber Science And Technology, Japan. Among these, carbon blacks such as HAF (High Abrasion Furnace), SAF (Super Abrasion Furnace), ISAF (Intermediate SAF), ISAF-HM (Intermediate SAF-High Modulus), FEF (Fast Extrusion Furnace), MAF, GPF (General Purpose Furnace), and SRF (Semi-Reinforcing Furnace) are preferred.

For a rubber composition for a tire tread, carbon black having a CTAB surface area of 40 to 250 m$^2$/g, a nitrogen adsorption specific surface area of 20 to 200 m$^2$/g, and a particle diameter of 10 to 50 nm is preferred, carbon black having a CTAB surface area of 70 to 180 m$^2$/g is more preferred, and a carbon black satisfying ASTM specification N110, N220, N234, N299, N326, N330, N330T, N339, N343, N351, or the like is preferred. Moreover, surface-treated carbon black having a surface to which 0.1 to 50% by weight of silica is applied is also preferred.

A combination of several fillers, such as a combination of carbon black and silica, is also effective; use of carbon black alone or a combination of carbon black and silica is preferred in a rubber composition for a tire tread.

In a rubber composition for a carcass or a side wall, carbon black having a CTAB surface area of 20 to 60 m$^2$/g and a particle diameter of 40 to 100 nm is preferred, and carbon black satisfying ASTM specification N330, N339, N343, N351, N550, N568, N582, N630, N642, N660, N662, N754, N762, or the like is preferred.

Silica having a CTAB specific surface area of 50 to 180 m$^2$/g and a nitrogen adsorption specific surface area of 50 to 300 m$^2$/g is preferred. As silica, commercially available products are preferably used, specifically, "AQ" and "AQ-N" manufactured by TOSOH SILICA CORPORATION, "ULTRASIL (registered trademark) VN3," "ULTRASIL (registered trademark) VN3-G," "ULTRASIL (registered trademark) 360," and "ULTRASIL (registered trademark) 7000" manufactured by Degussa AGC "Zeosil (registered trademark) 115GR," "Zeosil (registered trademark) 1115MP," "Zeosil (registered trademark) 1205MP," and "Zeosil (registered trademark) Z85MP" manufactured by Rhodia S.A., "Nipsil (registered trademark) AQ" manufactured by Nippon Silica Industries, and the like.

Moreover, silica having a pH of 6 to 8, silica containing 0.2 to 1.5% by weight of sodium, spherical silica having a circularity of 1 to 1.3, silica surface treated with silicone oil such as dimethylsilicone oil, an organic silicon compound having an ethoxysilyl group, silica surface treated with alcohol such as ethanol or polyethylene glycol, silica surface treated with an acidic compound such as phosphoric acid or maleic anhydride, or two or more silicas having different nitrogen adsorption specific surface areas may be compounded.

It is preferred that the amount of the filler to be used be within the range of 5 to 120 parts by weight relative to 100 parts by weight of the rubber component. If carbon black and silica are used in combination, it is preferred that 5 to 50 parts by weight of carbon black be compounded relative to 100 parts by weight of the rubber component, and it is preferred that the compounding ratio of silica/carbon black be preferably 0.7/1 to 1/0.1.

If silica is used as a filler, it is preferred that a compound having an element bondable to silica, such as silicon, or a functional group such as alkoxysilane, for example, a silane coupling agent such as bis(3-triethoxysilylpropyl)tetrasulfide ("Si-69" manufactured by Degussa AG), bis(3-triethoxysilylpropyl)disulfide ("Si-75" manufactured by Degussa AG), bis(3-diethoxymethylsilylpropyl)tetrasulfide, bis(3-diethoxymethylsilylpropyl)disulfide, S-[3-(tri ethoxysilyl)propyl]octanethioate ester ("NXT silane" manufactured by General Electronic Silicon Company), S-[3-{(2-methyl-1,3-propanedialkoxy)ethoxysilyl}propyl] octanethioate ester, and S-[3-((2-methyl-1,3-propanedialkoxy)methylsilyl)propyl]octanethioate ester phenyltriethoxysilane, methyltrimethoxysilane, methyltriethoxysilane, methyltriacetoxysilane, methyltributoxysilane, ethyltrimethoxysilane, ethyltriethoxysilane, isobutyltrimethoxysilane, isobutyltriethoxysilane, n-octyltrimethoxysilane, n-octyltriethoxysilane, vinyltrimethoxysilane, vinyltriethoxysilane, vinyltri(methoxyethoxy)silane, phenyltrimethoxysilane, phenyltriethoxysilane, phenyltriacetoxysilane, 3-methacryloxypropyltrimethoxysilane, 3-methacryloxy propyltriethoxysilane, 3-aminopropyltrimethoxysilane, 3-aminopropyltriethoxysilane, N-(2-aminoethyl)-3-aminopropyltrimethoxysilane, N-(2-aminoethyl)-3-aminopropyltriethoxysilane, (3-glycidoxypropyl)trimethoxysilane, (3-glycidoxypropyl)triethoxysilane, 2-(3,4-epoxycyclohexyl)ethyltrimethoxysilane, 2-(3,4-epoxycyclohexyl)ethyltriethoxysilane, 3-isocyanatepropyltrimethoxysilane, or 3-isocyanatepropyltriethoxysilane be added.

Among these compounds, bis(3-triethoxysilylpropyl)tetrasulfide ("Si-69" manufactured by Degussa AG), bis(3-triethoxysilylpropyl)disulfide ("Si-75" manufactured by Degussa AG), and 3-octanoylthiopropyltriethoxysilane ("NXT silane" manufactured by General Electronic Silicon Company) are preferred.

It is preferred that these compounds be compounded to rubber at the same time when silica is compounded, and the amount to be compounded is preferably 2 to 10% by weight, more preferably 7 to 9% by weight of silica.

The temperature when these compounds are compounded is preferably 80 to 200° C., more preferably 110 to 180° C.

If silica is used as a filler, monohydric alcohol such as ethanol, butanol, and octanol, di- or higher hydric alcohol such as ethylene glycol, diethylene glycol, triethylene glycol, polyethylene glycol, polypropylene glycol, pentaerythritol, and polyether polyol, N-alkylamine, amino acid, liquid polybutadiene whose molecular terminals are carboxyl modified or amine modified, or the like may be further compounded.

Examples of aluminum hydroxide include aluminum hydroxide having a nitrogen adsorption specific surface area of 5 to 250 m$^2$/g and an amount of DOP to be fed of 50 to 100 ml/100 g.

The sulfur component is, for example, at least one selected from the group consisting of powdered sulfur, precipitated sulfur, colloidal sulfur, insoluble sulfur, and highly dispersible sulfur. The sulfur component is preferably powdered sulfur. If the composition is used for a tire member containing a large amount of sulfur such as a member for a belt, insoluble sulfur is preferred.

Examples of a vulcanization accelerator different from the compound (X) include thiazole-based vulcanization accelerators, sulfenamide-based vulcanization accelerators, or guanidine-based vulcanization accelerators described in Gomu Kogyo Binran (Rubber Industrial Handbook <Fourth edition>, pp. 412 to 413 (published by the Society of Rubber Science And Technology, Japan, January 20, Heisei 6).

Examples of the vulcanization accelerator different from the compound (X) specifically include N-cyclohexyl-2-benzothiazolylsulfenamide (CBS), N-tert-butyl-2-benzothiazolylsulfenamide (BBS), N,N-dicyclohexyl-2-benzothiazolylsulfenamide (DCBS), 2-mercaptobenzothiazole (MBT), dibenzothiazyl disulfide (MBTS), and diphenylguanidine (DPG).

If the filler is carbon black, a combination of N-cyclohexyl-2-benzothiazolylsulfenamide (CBS), N-tert-butyl-2-benzothiazolylsulfenamide (BBS), N,N-dicyclohexyl-2-benzothiazolylsulfenamide (DCBS), or dibenzothiazyl disulfide (MBTS) with diphenylguanidine (DPG) is preferred as the vulcanization accelerator different from the compound (X). If the filler is a combination of silica and carbon black, a combination of N-cyclohexyl-2-benzothiazolylsulfenamide (CBS), N-tert-butyl-2-benzothiazolylsulfenamide (BBS), N,N-dicyclohexyl-2-benzothiazolylsulfenamide (DCBS) or dibenzothiazyl disulfide (MBTS) with diphenylguanidine (DPG) is preferred as the vulcanization accelerator different from the compound (X).

It is preferred that the mixing ratio of sulfur (A) to the total amount (B) of the vulcanization accelerator and the vulcanization aid be A/B=2/1 to 1/2 in terms of the weight ratio. If particularly heat resistance is enhanced in a rubber member mainly composed of natural rubber, it is preferred that A/B be 1 or less (EV vulcanization).

In kneading, usually, the rubber component and the filler are kneaded (hereinafter, referred to as "Procedure 1" in some cases), and the kneaded product obtained in Procedure 1 and the sulfur component are further kneaded (hereinafter, referred to as "Procedure 2" in some cases). Both the kneaded product obtained in Procedure 1 and the kneaded product obtained in Procedure 2 are the rubber composition according to the present embodiment.

Although the compound (X) may be compounded in Procedure 2, it is preferred that the compound (X) be compounded in Procedure 1 with the filler and zinc oxide. The amount of the compound (X) to be used is within the range of preferably 0.1 to 10 parts by weight, more preferably 0.3 to 3 parts by weight relative to 100 parts by weight of the rubber component.

The compounding temperature when the compound (X) is compounded in Procedure 1 is preferably 80 to 200° C., more preferably 110 to 180° C. It is preferred that the compounding temperature when the compound (X) is compounded in Procedure 2 be 50 to 100° C.

The compound (X) can be preliminarily compounded with a carrier. Examples of such a carrier include the fillers listed above, and "inorganic fillers and reinforcing agents" described in "Gomu Kogyo Binran (Rubber Industrial Handbook) <Fourth edition>," pp. 510 to 513, edited by the Society of Rubber Science And Technology, Japan. Among these, carbon black, silica, calcined clay, and aluminum hydroxide are preferred. It is preferred that the amount of such a carrier to be compounded be 10 to 1000 parts by weight relative to 100 parts by weight of the compound (X).

If the melting point of the compound (X) is high, it is preferred that the compound (X) be pulverized into particles having a particle size of 100 µm or less to ensure sufficient dispersibility during kneading.

Specifically, the compound (X) and carbon black, silica, calcined clay, or aluminum hydroxide can be mixed, and the resulting mixture can be pulverized to produce particles containing the compound (X) and having a particle size of 100 µm or less.

An agent for improving viscoelasticity properties usually used in the rubber field can also be compounded and kneaded. Examples of such an agent include silane coupling agents such as N,N'-bis(2-methyl-2-nitropropyl)-1,6-hexanediamine ("SUMIFINE (registered trademark) 1162" manufactured by Sumitomo Chemical Co., Ltd.), the dithiouracil compounds described in JP 63-23942 A, nitrosoquinoline compounds such as 5-nitroso-8-hydroxyquinoline (NQ-58) described in JP 60-82406 A, "TACKIROL (registered trademark) AP and V-200" manufactured by TAOKA CHEMICAL COMPANY, LIMITED, alkylphenol-sulfur chloride condensates described in JP 2009-138148 A such as "Vultac 2, 3, 4, 5, 7, and 710" manufactured by Pennwalt Corporation, bis(3-triethoxysilylpropyl)tetrasulfide ("Si-69" manufactured by Degussa AG), bis(3-triethoxysilylpropyl)disulfide ("Si-75" manufactured by Degussa AG), bis(3-diethoxymethylsilylpropyl)tetrasulfide, bis(3-diethoxymethylsilylpropyl)disulfide, S-[3-(triethoxysilyl)propyl] octanethioate ester, S-[3-{(2-methyl-1,3-propanedialkoxy)ethoxysilyl}propyl] octanethioate ester, and S-[3-({(2-methyl-1,3-propanedialkoxy)methylsilyl}propyl] octanethioate ester phenyltriethoxysilane, methyltrimethoxysilane, methyltriethoxysilane, methyltriacetoxysilane, methyltributoxysilane, ethyltrimethoxysilane, ethyltriethoxysilane, isobutyltrimethoxysilane, isobutyltriethoxysilane, n-octyltrimethoxysilane, n-octyltriethoxysilane, vinyltrimethoxysilane, vinyltriethoxysilane, vinyltri(methoxyethoxy)silane, phenyltrimethoxysilane, phenyltriethoxysilane, phenyltriacetoxysilane, 3-methacryloxypropyltrimethoxysilane, 3-methacryloxypropyltriethoxysilane, 3-aminopropyltrimethoxysilane, 3-aminopropyltriethoxysilane, N-(2-aminoethyl)-3-aminopropyltrimethoxysilane, N-(2-aminoethyl)-3-aminopropyltriethoxysilane, (3-glycidoxypropyl)trimethoxysilane, (3-glycidoxypropyl)triethoxysilane, 2-(3,4-epoxycyclohexyl)ethyltrimethoxysilane, 2-(3,4-epoxycyclohexyl)ethyltriethoxysilane, 3-isocyanatepropyltrimethoxysilane, and 3-isocyanatepropyltriethoxysilane; 1,6-bis(N,N'-dibenzylthiocarbamoyldithio)hexane ("KA9188" manufactured by Bayer AG); 1,6-hexamethylenedithiosulfate disodium salt dihydrate; 1,3-bis(citraconimidemethyl)benzene ("Perkalink 900" manufactured by Flexsys America LP); carboxylic hydrazide derivatives such as 1-benzoyl-2-phenylhydrazide, 1- or 3-hydroxy-N'-(1-methylethylidene)-2-naphthoic hydrazide, 1- or 3-hydroxy-N'-(1-methylpropylidene)-2-naphthoic hydrazide described in JP 2004-91505 A, 1- or 3-hydroxy-N'-(1,3-dimethylbutylidene)-2-naphthoic hydrazide, and 1- or 3-hydroxy-N'-(2-furylmethylene)-2-naphthoic hydrazide; 3-hydroxy-N'-(1,3-dimethylbutylidene)-2-naphthoic hydrazide, 3-hydroxy-N'-(1,3-diphenylethylidene)-2-naphthoic hydrazide, and 3-hydroxy-N'-(1-methylethylidene)-2-naphthoic hydrazide described in JP 2000-190704 A; bismercaptooxadiazole compounds described in JP 2006-328310 A; pyrithione salt compounds described in JP 2009-40898 A; and cobalt hydroxide compounds described in JP 2006-249361 A.

Among these agents for improving viscoelasticity properties, N,N'-bis(2-methyl-2-nitropropyl)-1,6-hexanediamine ("SUMIFINE (registered trademark) 1162" manufactured by Sumitomo Chemical Co., Ltd.), 5-nitroso-8-hydroxyquinoline (NQ-58), bis(3-triethoxysilylpropyl)tetrasulfide ("Si-69" manufactured by Degussa AG), bis(3-triethoxysilylpropyl)disulfide ("Si-75" manufactured by Degussa AG), 1,6-bis(N,N'-dibenzylthiocarbamoyldithio)-hexane ("KA9188" manufactured by Bayer AG), hexamethylenebisthiosulfate disodium salt dihydrate, 1,3-bis(citraconimidemethyl)benzene ("Perkalink 900" manufactured by Flexsys America LP), and alkylphenol-sulfur chloride condensates such as "TACKIROL (registered trademark) AP and V-200" manufactured by TAOKA CHEMICAL COMPANY, LIMITED are preferred.

It is preferred that zinc oxide be compounded in Procedure 1, and it is preferred that a vulcanization accelerator be compounded in Procedure 2.

A variety of compounding agents usually used in the rubber field can be compounded, and be kneaded. Examples of such compounding agents include antioxidants; oils; fatty acids such as stearic acid; coumarone-indene resin such as a coumarone resin NG4 (softening point: 81 to 100° C.) manufactured by Nippon Steel Chemical K.K., and a process resin AC5 (softening point: 75° C.) manufactured by KOBE OIL CHEMICAL INDUSTRIAL Co., Ltd.; terpene-based resins such as terpene resins, terpene-phenol resins, and aromatic-modified terpene resins; rosin derivatives such as "NIKANOL (registered trademark) A70" (softening point: 70 to 90° C.) manufactured by Mitsubishi Gas Chemical Company, Inc.; hydrogenating rosin derivatives; novolac alkylphenol resins; resol alkylphenol resins; C5-based petroleum resins; and liquid polybutadienes. These compounding agents may be compounded in either of Procedure 1 and Procedure 2.

Examples of the oils include process oils and vegetable fats and oils. Examples of the process oils include paraffin-based process oils, naphthene-based process oils, and aromatic process oils, and specifically include aromatic oils ("NC-140" manufactured by Cosmo Oil Co., Ltd.), and process oils ("Diana process PS32" manufactured by Idemitsu Kosan Co., Ltd.).

Examples of the antioxidants include those described in "Gomu Kogyo Binran (Rubber Industrial Handbook) <Fourth edition>," pp. 436 to 443, edited by the Society of Rubber Science And Technology, Japan. Among these antioxidants, N-phenyl-N'-1,3-dimethylbutyl-p-phenylenediamine (6PPD), a reaction product (TMDQ) of aniline and acetone, poly(2,2,4-trimethyl-1,2-)dihydroquinoline) ("Antioxidant FR" manufactured by Songwon Industrial Co., Ltd.), synthetic waxes (such as paraffin wax), vegetable wax, and "Antigen (registered trademark) 6C" manufactured by Sumitomo Chemical Co., Ltd. are preferred.

Examples of the waxes include "SUNNOC (registered trademark) wax" manufactured by Ouchi Shinko Chemical Industrial Co., Ltd., and "OZOACE-0355" manufactured by NIPPON SEIRO CO., LTD.

A vulcanizing agent usually used in the rubber field, such as morpholine disulfide, can also be compounded, and be kneaded. It is preferred that these vulcanizing agents be compounded in Procedure 2.

Moreover, a peptizing agent or a retarder may be compounded, and be kneaded; furthermore, a variety of typical rubber chemicals, softening agents, and the like may be compounded, and be kneaded when necessary.

Examples of the retarder include phthalic anhydride, benzoic acid, salicylic acid, N-nitrosodiphenylamine, N-(cyclohexylthio)-phthalimide (CTP), sulfonamide derivatives, diphenylurea, and bis(tridecyl)pentaerythritol-diphosphate; N-(cyclohexylthio)-phthalimide (CTP) is preferred.

Although the retarder may be compounded, and be kneaded in Procedure 1, it is preferred that the retarder be compounded, and be kneaded in Procedure 2.

The amount of the retarder to be used is preferably 0.01 to 1 part by weight, more preferably 0.05 to 0.5 parts by weight relative to 100 parts by weight of the rubber component.

The rubber composition obtained in Procedure 2 is heat treated to obtain a vulcanized rubber according to the present embodiment.

As the temperature condition for such a heat treatment, 120 to 180° C. is preferred. The heat treatment is usually performed under normal pressure or increased pressure.

The vulcanized rubber in the present embodiment includes a vulcanized rubber obtained through a heat treatment of a rubber composition processed into a specific state.

Here, in the tire field, examples of the "rubber composition processed into a specific state" include "rubber compositions applied onto steel cords," "rubber compositions applied onto carcass fiber cords," and "rubber compositions processed into shapes for members for treads." Moreover, the members obtained through a heat treatment of these rubber compositions, such as belts, carcasses, inner liners, side walls, and treads (cap treads or undertreads) are usually further molded into a tire shape with other members by the method usually performed in the tire field. Namely, the rubber composition is integrated in a tire, and is heat treated in a state of a green tire containing the rubber composition. Such a heat treatment is usually performed under increased pressure.

The vulcanized rubber thus obtained is used to produce a tire by a typical method. Namely, a rubber composition before vulcanization processing is extruded into a member for a tread; the member for a tread is bonded, and is molded on a tire molding machine by a typical method to form a green tire; the green tire is heated under increased pressure in a vulcanizing machine to obtain a tire. Namely, the tire according to the present embodiment includes a rubber member containing a vulcanized rubber obtained through a heat treatment of the rubber composition. The rubber member included in the tire may be applied onto a steel cord or a carcass fiber cord, or may be a tread.

Examples of the tire include pneumatic tires and solid tires.

Examples of applications of the vulcanized rubber in the present invention include applications to tires, applications to vibration proof rubber, applications to rubber belts, applications to vibration control agents, and applications to seismic isolation rubber. Examples of the applications to vibration proof rubber include vibration proof rubbers for vehicles such as engine mounts, strut mounts, bushes, and exhaust hangers. The vibration proof rubber is usually obtained by processing a kneaded product of a rubber composition into a shape of vibration proof rubber, and then performing a heat treatment. Examples of the applications to rubber belts include transmission belts, conveyor belts, and V belts.

EXAMPLES

Hereinafter, the present invention will be specifically described by way of Examples and Test Examples.

Example 1

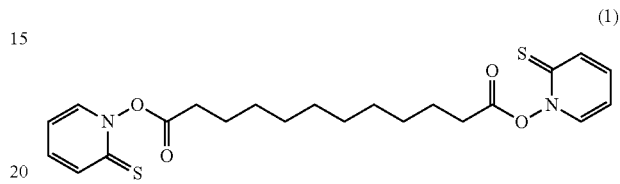

2-Mercaptopyridine N-oxide (50 g) was added to a solution of dodecanedioyl dichloride (53 g) in chloroform cooled to −78° C. Pyridine (31 g) was further added dropwise at the same temperature as above, and the resulting mixture was then stirred at 0° C. for 1 hour. The reaction was quenched with water, and extraction with chloroform, washing with brine, drying with anhydrous sodium sulfate, and distillation off of the solvent under reduced pressure were performed. The resulting residue was recrystallized with chloroform/hexane to obtain a compound represented by the above formula (1) (68 g, yield: 77%).

$^1$H-NMR (CDCl$_3$, 270 MHz) δ ppm: 1.32-1.44 (12H, m), 1.77-1.88 (4H, m), 2.72 (4H, t, J=7.6 Hz), 6.63 (2H, ddd, J=6.8 Hz, 6.8 Hz, 1.6 Hz), 7.21 (2H, ddd, J=8.6 Hz, 6.8 Hz, 1.9 Hz), 7.56 (2H, dd, J=6.8 Hz, 1.6 Hz), 7.69 (2H, dd, J=8.6 Hz, 1.9 Hz).

Example 2

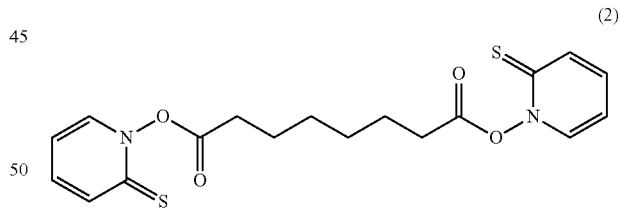

2-Hydroxypyridine N-oxide (5.0 g) was added to a solution of suberoyl chloride (4.1 g) in dichloromethane cooled to −70° C. Pyridine (3.1 g) was further added dropwise at the same temperature as above, and the resulting mixture was then stirred for 2 hours, and was further stirred at 0° C. for 2 hours. The reaction was quenched with water, and extraction with dichloromethane, washing with brine, drying with anhydrous sodium sulfate, and distillation off of the solvent under reduced pressure were performed. The resulting residue was recrystallized to obtain a compound represented by the above formula (2) (6.5 g, yield: 84%).

$^1$H-NMR (CDCl$_3$, 270 MHz) δ ppm: 1.25-1.86 (8H, m), 2.74 (4H, t, J=4.9 Hz), 6.63-6.66 (2H, m), 7.20-7.27 (2H, m), 7.59-7.75 (4H, m).

Example 3

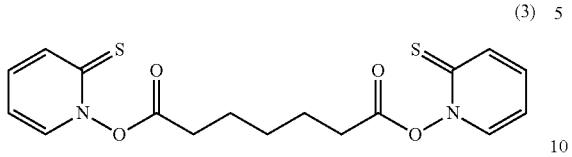

(3)

12 g of 2-mercaptopyridine N-oxide and 18 g of 1-ethyl-3-(3-dimethylaminopropyl)carbodiimide hydrochloride were added to a solution obtained by mixing 5 g of pimelic acid and chloroform, and were stirred at room temperature for 10 hours. 60 mL of water was added to the resulting reaction mixture, and the reaction mixture was separated to obtain an organic layer and an aqueous layer. The resulting aqueous layer was further extracted with ethyl acetate to obtain an organic layer. The resulting organic layers were combined, and were dried with anhydrous sodium sulfate; the solvent was removed by distillation off under reduced pressure to obtain a crude product. The resulting crude product was refined by silica gel column chromatography (ethyl acetate/hexane: 50%-80%-90%), and was further recrystallized with ethyl acetate/hexane to obtain 6.9 g of a compound represented by the above formula (3). The yield was 57%.

$^1$H-NMR (CDCl$_3$, 400 MHz) δ ppm: 1.59-1.65 (2H, m), 1.86-1.94 (4H, m), 2.76 (4H, t, J=7.1 Hz), 6.62-6.65 (2H, m), 7.18-7.27 (2H, m), 7.56-7.61 (2H, m), 7.68-7.70 (2H, m).

Example 4

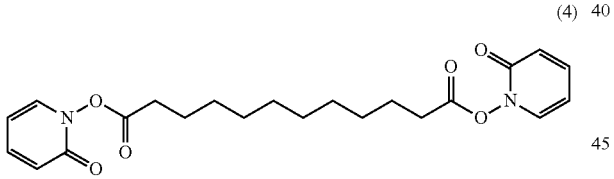

(4)

Dodecanedioic acid (10 g) and thionyl chloride (13 g) were mixed at 60° C. for 2 hours. After it was checked that solids were dissolved, non-reacted thionyl chloride was distilled off from the resulting mixture under reduced pressure. Subsequently, the operation to further add anhydrous toluene to the mixture, and distill off under reduced pressure was repeated twice to obtain bis(acid chloride) (20).

2-Hydroxypyridine N-oxide (11 g) was added to a solution of bis(acid chloride) (20) (12 g) in chloroform, and was then cooled to 0° C. Triethylamine (10 g) was further added dropwise at the same temperature as above, and the resulting mixture was then stirred at room temperature for 1 hour. The reaction was quenched with an aqueous solution of saturated sodium hydrogen carbonate, and extraction with chloroform, washing with brine, drying with Na$_2$SO$_4$, and distillation off of the solvent under reduced pressure were performed. The resulting crude product was recrystallized with ethyl acetate/hexane to obtain a compound represented by the above formula (4) (6.6 g, yield: 37%) as a white solid.

$^1$H-NMR (CDCl$_3$, 400 MHz) δ ppm: 1.29-1.45 (12H, m), 1.57-1.63 (4H, m), 2.65 (4H, t, J=7.6 Hz), 6.18 (2H, ddd, J=6.8 Hz, 6.8 Hz, 1.7 Hz), 6.71-6.74 (2H, m), 7.31-7.39 (4H, m).

Example 5

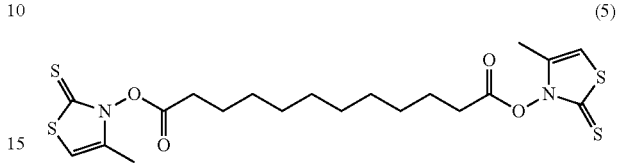

(5)

Dodecanedioic acid (13 g), dichloromethane (120 mL), and dimethylformamide (0.31 g) were mixed, and were cooled to 0° C. Oxalyl chloride (9.6 g) was added to the resulting mixture over 20 minutes, and was further stirred at room temperature for 2 hours. The resulting mixture was dried under reduced pressure to obtain bis(acid chloride) (21).

Thiohydroxamic acid (16 g), pyridine (7.2 g), and dichloromethane (120 mL) were mixed, and were cooled to 0° C. A solution of bis(acid chloride) (21) in dichloromethane was added dropwise to the resulting mixture over 30 minutes, and was further stirred at room temperature for 2 hours. 1 mol/L Hydrochloric acid was added to the resulting reaction mixture to make the mixture acidic, and the mixture was further stirred for 20 minutes. The resulting reaction mixture was dried through condensation, and was refined by silica gel column chromatography to obtain a compound represented by the above formula (5) (21 g, yield: 75%) as a light brown oil.

$^1$H-NMR (CDCl$_3$, 270 MHz) δ ppm: 1.25-1.45 (12H, m), 1.80-1.83 (4H, m), 2.16 (6H, s), 2.64-2.76 (4H, m), 6.24 (2H, s).

Example 6

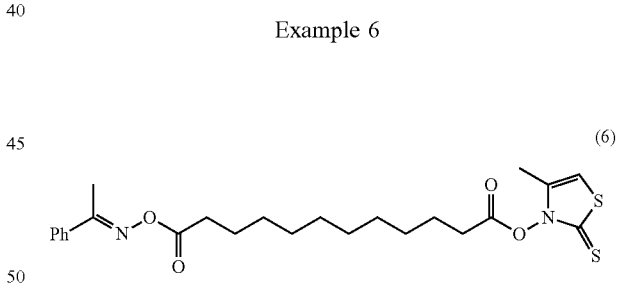

(6)

Acetophenone (50 g), ethanol (500 mL), and hydroxylamine hydrochloride (29 g) were mixed, and were cooled to 0° C. An aqueous solution (100 mL) of sodium hydroxide (18 g) was added dropwise to the resulting mixture over 30 minutes, and was further stirred at room temperature overnight. Ethanol was distilled off from the resulting reaction mixture, and the mixture was then cooled to 0° C.; 1 mol/L hydrochloric acid was added to the mixture to adjust the pH of the reaction mixture to 3 to 4. A white precipitate precipitated through stirring of the resulting mixture for 10 minutes was filtered, and was further washed with water. The resulting white precipitate was dried to obtain acetophenone oxime (40 g, yield: 71%) as a white solid.

1-Ethyl-3-(3-dimethylaminopropyl)carbodiimide hydrochloride (42 g) was added to a 0° C. solution of dodecanedioic acid (50 g) in dichloromethane, and was stirred at room temperature for 30 minutes. The resulting mixture was cooled to 0° C.; a solution of acetophenone oxime (29 g) in dichloromethane was added dropwise to the mixture, and was stirred at room temperature overnight. The reaction was quenched with water, and extraction with dichloromethane, drying with anhydrous sodium sulfate, and distillation off of the solvent under reduced pressure were performed. The resulting crude product was refined by silica gel column chromatography (ethyl acetate/hexane) to obtain monooxime ester (25) (40 g, yield: 27%) as a white solid.

Oxalyl chloride (8.0 g) was added dropwise over 30 minutes to a solution of monooxime ester (25) (22 g) in dichloromethane cooled to 0° C., and the resulting mixture was then stirred at room temperature for 1 hour. The resulting reaction mixture was dried and solidified through condensation to obtain the target monoacid chloride (26) as a light yellow oil.

Thiohydroxamic acid (9.3 g) and a solution of pyridine (10 g) in dichloromethane were added to a solution of monoacid chloride (26) in dichloromethane cooled to 0° C., and the resulting mixture was stirred at room temperature for 3 hours. The resulting reaction mixture was cooled to 0 to 5° C., and 1 mol/L hydrochloric acid was then added to the mixture to make the reaction mixture acidic. The acidic reaction mixture was separated, and an aqueous solution of saturated sodium hydrogen carbonate was added to the resulting organic layer; further, the solution was separated, and was washed to obtain an organic layer. Moreover, the aqueous layer obtained through separation was further extracted with dichloromethane to obtain an organic layer. The resulting organic layers were combined, and the solvent was distilled off under reduced pressure; the resultant was refined by silica gel column chromatography to obtain a compound represented by the above formula (6) (16 g, yield: 52%).

$^1$H-NMR (DMSO, 270 MHz) δ ppm: 1.25-1.40 (12H, m), 1.58-1.69 (4H, m), 2.12 (3H, s), 2.35 (3H, s), (2H, m), 2.66-2.74 (2H, m), 6.81 (1H, s), 7.46-7.52 (3H, m), 7.76-7.77 (2H, m).

Example 7

Procedure 1

Using a Banbury mixer (600-ml Labo Plastomill manufactured by Toyo Seiki Seisaku-sho, Ltd.), 100 parts by weight of natural rubber (RSS#1), 45 parts by weight of HAF (manufactured by Asahi Carbon Co., Ltd., trade name "Asahi #70"), 3 parts by weight of stearic acid, 5 parts by weight of zinc oxide, 1 part by weight of an antioxidant (N-phenyl-N'-1,3-dimethylbutyl-p-phenylenediamine (6PPD): trade name "Antigen (registered trademark) 6C" manufactured by Sumitomo Chemical Co., Ltd.), and 1 part by weight of the compound represented by the formula (1) and obtained in Example 1 above were kneaded to obtain a kneaded product. In the step, kneading was performed at the setting temperature of the mixer of 120° C. and the number of rotations of the mixer of 50 rpm for 5 minutes after a variety of chemicals and a filler were placed. The temperature of the kneaded product when kneading was completed was 166° C.

Procedure 2

In an open roll mill in which a roll setting temperature was 60° C., the kneaded product obtained in Procedure 1, 1 part by weight of a vulcanization accelerator N-cyclohexyl-2-benzothiazolesulfenamide (CBS), and 2 parts by weight of sulfur were kneaded and compounded to obtain an unvulcanized rubber composition.

Reference Example 1

An unvulcanized rubber composition was obtained in the same manner as in Example 7 except that in Example 7, the compound represented by the formula (1) was not used. The temperature of the kneaded product when kneading was completed in Procedure 1 was 160° C.

Example 8

As described below, the vulcanization curve of the unvulcanized rubber composition obtained in Procedure 2 in Example 7 was measured, and the vulcanizing rate and the reversion rate were calculated.

(1) Vulcanization Curve

The vulcanization curve was measured with a rotorless rheometer RLR-4 manufactured by Toyo Seiki Seisaku-sho, Ltd.

Conditions: temperature: 145° C. (vulcanizing rate), 190° C. (reversion rate)

angle of vibration: 1.0 deg., the number of vibrations: 100 cpm (2) Vulcanizing Rate From the result obtained from (1), the vulcanizing rate was calculated from the expression (50) using a time to reach 10% vulcanization (T10) and a time to reach 90% vulcanization (T90). A smaller value indicates the time from the start of vulcanization to the end thereof is shorter, unevenness of vulcanization is barely generated, and vulcanization properties are higher.

vulcanizing rate (min)=$T$90 (min)–$T$10 (min)    expression (50)

(3) Reversion Rate

From the result obtained from (1), the torque increasing value (M(15)–ML) after 15 minutes from the start of vulcanization was expressed as a relative value to the torque increasing value (MH–ML), which was defined as 100, and the reversion rate was determined as a value obtained by subtracting the torque increasing value (M(15)–ML) from 100. A smaller value indicates that reversion is more reduced, and vulcanization properties are higher. MH indicates the maximum torque value while ML indicates the minimum torque value.

reversion rate=100–{[$M$(15)–$ML$]/[$MH$–$ML$]}×100

When the unvulcanized rubber composition obtained in Reference Example 1 was used as a control, the vulcanizing rate of the unvulcanized rubber composition obtained in Procedure 2 in Example 7 was enhanced by 35%, and the reversion rate was reduced by 21 points.

Example 9

An unvulcanized rubber composition was obtained in the same manner as in Example 7 except that in Example 7, the compound represented by the formula (1) in Example 1 was replaced with the compound represented by the formula (2) in Example 2. The temperature of the kneaded product when kneading was completed in Procedure 1 was 168° C.

Example 10

The measurement was performed in the same manner as in Example 8; when the unvulcanized rubber composition obtained in Reference Example 1 was used as a control, the vulcanizing rate of the unvulcanized rubber composition obtained in Procedure 2 in Example 9 was enhanced by 27%, and the reversion rate was reduced by 19 points.

Example 11

An unvulcanized rubber composition was obtained in the same manner as in Example 7 except that in Example 7, the compound represented by the formula (1) in Example 1 was replaced with the compound represented by the formula (3) in Example 3. The temperature of the kneaded product when kneading was completed in Procedure 1 was 168° C.

Example 12

The measurement was performed in the same manner as in Example 8; when the unvulcanized rubber composition obtained in Reference Example 1 was used as a control, the vulcanizing rate of the unvulcanized rubber composition obtained in Procedure 2 in Example 11 was enhanced by 34%, and the reversion rate was reduced by 21 points.

Example 13

Procedure 1

Using a Banbury mixer (600-ml Labo Plastomill manufactured by Toyo Seiki Seisaku-sho, Ltd.), 100 parts by weight of natural rubber (RSS#1), 45 parts by weight of HAF (manufactured by Asahi Carbon Co., Ltd., trade name "Asahi #70"), 3 parts by weight of stearic acid, 5 parts by weight of zinc oxide, and 1 part by weight of an antioxidant (N-phenyl-N'-1,3-dimethylbutyl-p-phenylenediamine (6PPD): trade name "Antigen (registered trademark) 6C" manufactured by Sumitomo Chemical Co., Ltd.) were kneaded to obtain a kneaded product. In the step, kneading was performed at the setting temperature of the mixer of 120° C. and the number of rotations of the mixer of 50 rpm for 5 minutes after a variety of chemicals and a filler were placed. The temperature of the kneaded product when kneading was completed was 150° C.

Procedure 2

In an open roll mill in which a roll setting temperature was 60° C., the kneaded product obtained in Procedure 1, 1 part by weight of the compound represented by the formula (4) and obtained in Example 4 above, 1 part by weight of a vulcanization accelerator N-cyclohexyl-2-benzothiazole-sulfenamide (CBS), and 2 parts by weight of sulfur were kneaded to obtain an unvulcanized rubber composition.

Example 14

The measurement was performed in the same manner as in Example 8; when the unvulcanized rubber composition obtained in Reference Example 1 was used as a control, the vulcanizing rate of the unvulcanized rubber composition obtained in Procedure 2 in Example 13 was enhanced by 12%, and the reversion rate was reduced by 9 points.

Example 15

An unvulcanized rubber composition was obtained in the same manner as in Example 7 except that in Example 7, the compound represented by the formula (1) in Example 1 was replaced with the compound represented by the formula (5) in Example 5. The temperature of the kneaded product when kneading was completed in Procedure 1 was 165° C.

Example 16

The measurement was performed in the same manner as in Example 8; when the unvulcanized rubber composition obtained in Reference Example 1 was used as a control, the vulcanizing rate of the unvulcanized rubber composition obtained in Procedure 2 in Example 15 was enhanced by 25%, and the reversion rate was reduced by 8 points.

Example 17

An unvulcanized rubber composition was obtained in the same manner as in Example 7 except that in Example 7, the compound represented by the formula (1) in Example 1 was replaced with the compound represented by the formula (6) in Example 6. The temperature of the kneaded product when kneading was completed in Procedure 1 was 165° C.

Example 18

The measurement was performed in the same manner as in Example 8; when the unvulcanized rubber composition obtained in Reference Example 1 was used as a control, the vulcanizing rate of the unvulcanized rubber composition obtained in Procedure 2 in Example 17 was enhanced by 27%, and the reversion rate was reduced by 7 points.

The results when the compounds represented by the formulae (1) to (6) were used are shown in Table 1. In the table, the vulcanizing rate and the reversion rate indicate relative values where the results of Reference Example 1 are 1.

TABLE 1

|  | Reference Example 1 | Example 8 | Example 10 | Example 12 | Example 14 | Example 16 | Example 18 |
| --- | --- | --- | --- | --- | --- | --- | --- |
| Compound | — | (1) | (2) | (3) | (4) | (5) | (6) |
| Vulcanizing rate | 1 | 0.65 | 0.73 | 0.66 | 0.88 | 0.75 | 0.73 |
| Reversion rate | 1 | 0.58 | 0.59 | 0.58 | 0.79 | 0.82 | 0.84 |

Example 19

Procedure 1

Using a Banbury mixer (600-ml Labo Plastomill manufactured by Toyo Seiki Seisaku-sho, Ltd.), 100 parts by weight of butadiene rubber (BR01), 45 parts by weight of HAF (manufactured by Asahi Carbon Co., Ltd., trade name "Asahi #70"), 3 parts by weight of stearic acid, 5 parts by weight of zinc oxide, 1 part by weight of an antioxidant (N-phenyl-N'-1,3-dimethylbutyl-p-phenylenediamine (6PPD): trade name "Antigen (registered trademark) 6C" manufactured by Sumitomo Chemical Co., Ltd.), and 1 part by weight of the compound represented by the formula (1) in Example 1 were kneaded to obtain a kneaded product. In the step, kneading was performed at the setting temperature of the mixer of 140° C. and the number of rotations of the mixer of 50 rpm for 5 minutes after a variety of chemicals and a filler were placed. The temperature of the kneaded product when kneading was completed was 160° C.

Procedure 2

In an open roll mill in which a roll setting temperature was 60° C., the kneaded product obtained in Procedure 1, 1 part by weight of a vulcanization accelerator N-cyclohexyl-2-benzothiazolesulfenamide (CBS), and 2 parts by weight of sulfur were kneaded and compounded to obtain an unvulcanized rubber composition.

Reference Example 2

An unvulcanized rubber composition was obtained in the same manner as in Example 19 except that in Example 19, the compound represented by the formula (1) in Example 1 was not used. The temperature of the kneaded product when kneading was completed in Procedure 1 was 158° C.

Example 20

As described below, the vulcanization curve of the unvulcanized rubber composition obtained in Procedure 2 in Example 19 was measured, and the vulcanizing rate was calculated.
(1) Vulcanization Curve
The vulcanization curve was measured with a rotorless rheometer RLR-4 manufactured by Toyo Seiki Seisaku-sho, Ltd.
Conditions: temperature: 145° C. (vulcanizing rate), 190° C. (reversion rate)
angle of vibration: 1.0 deg., the number of vibrations: 100 cpm
(2) Vulcanizing Rate
From the result obtained from (1), the vulcanizing rate was calculated from the expression (50) using T10 and T90. A smaller value indicates the time from the start of vulcanization to the end thereof is shorter, unevenness of vulcanization is barely generated, and vulcanization properties are higher.

$$\text{vulcanizing rate (min)}=T90\text{ (min)}-T10\text{ (min)} \quad \text{expression (50)}$$

When the unvulcanized rubber composition obtained in Reference Example 2 was used as a control, the vulcanizing rate of the unvulcanized rubber composition obtained in Procedure 2 in Example 19 was enhanced by 33%.

The result when the compound represented by the formula (1) was used is shown in Table 2. In the table, the vulcanizing rate indicates a relative value where the result of Reference Example 2 is 1.

TABLE 2

|  | Reference Example 2 | Example 20 |
| --- | --- | --- |
| Compound | — | (1) |
| Vulcanizing rate | 1 | 0.67 |

Example 21

An unvulcanized rubber composition was obtained in the same manner as in Example 19 except that in Example 19, polybutadiene rubber BR01 (manufactured by JSR Corporation) was replaced with styrene-butadiene copolymerized rubber SBR#1502 (manufactured by JSR Corporation). The temperature of the kneaded product when kneading was completed in Procedure 1 was 162° C.

Reference Example 3

An unvulcanized rubber composition was obtained in the same manner as in Example 21 except that in Example 21, the compound represented by the formula (1) in Example 1 was not used. The temperature of the kneaded product when kneading was completed in Procedure 1 was 161° C.

Example 22

The measurement was performed in the same manner as in Example 20; when the unvulcanized rubber composition obtained in Reference Example 3 was used as a control, the vulcanizing rate of the unvulcanized rubber composition obtained in Procedure 2 in Example 21 was enhanced by 29%.

The result when the compound represented by the formula (1) was used is shown in Table 3. In the table, the vulcanizing rate indicates a relative value where the result of Reference Example 3 is 1.

TABLE 3

|  | Reference Example 3 | Example 22 |
| --- | --- | --- |
| Compound | — | (1) |
| Vulcanizing rate | 1 | 0.71 |

Example 23

An unvulcanized rubber composition was obtained in the same manner as in Example 21 except that in Example 21, 45 parts by weight of HAF (manufactured by Asahi Carbon Co., Ltd., trade name "Asahi #70") was replaced with 40 parts by weight of hydrous silica ("Nipsil (registered trademark) AQ" manufactured by TOSOH SILICA CORPORATION). The temperature of the kneaded product when kneading was completed in Procedure 1 was 162° C.

Reference Example 4

An unvulcanized rubber composition was obtained in the same manner as in Example 23 except that in Example 23, the compound represented by the formula (1) in Example 1 was not used. The temperature of the kneaded product when kneading was completed in Procedure 1 was 163° C.

Example 24

The measurement was performed in the same manner as in Example 20; the unvulcanized rubber composition obtained in Reference Example 4 was used as a control, the vulcanizing rate of the unvulcanized rubber composition obtained in Procedure 2 in Example 23 was enhanced by 62%.

The result when the compound represented by the formula (1) was used is shown in Table 4. In the table, the vulcanizing rate indicates a relative value when the result of Reference Example 4 is 1.

TABLE 4

|  | Reference Example 4 | Example 24 |
| --- | --- | --- |
| Compound | — | (1) |
| Vulcanizing rate | 1 | 0.38 |

Example 25

Procedure 1

Using a Banbury mixer (600-ml Labo Plastomill manufactured by Toyo Seiki Seisaku-sho, Ltd.), 100 parts by weight of ethylene-propylene-diene copolymerized rubber EPDM505A (manufactured by Sumitomo Chemical Co., Ltd.), 60 parts by weight of FEF (manufactured by Asahi Carbon Co., Ltd., trade name "Asahi #60"), 1 part by weight of stearic acid, 5 parts by weight of zinc oxide, and 1 part by weight of the compound represented by the formula (1) and obtained in Example 1 above were kneaded to obtain a kneaded product. In the step, kneading was performed at the setting temperature of the mixer of 130° C. and the number of rotations of the mixer of 50 rpm for 5 minutes after a variety of chemicals and a filler were placed. The temperature of the kneaded product when kneading was completed was 164° C.

Procedure 2

In an open roll mill in which a roll setting temperature was 60° C., the kneaded product obtained in Procedure 1, 1 part by weight of a vulcanization accelerator N-t-butyl-2-benzothiazolesulfenamide (BBS), and 2.8 parts by weight of sulfur were kneaded and compounded to obtain an unvulcanized rubber composition.

Reference Example 5

An unvulcanized rubber composition was obtained in the same manner as in Example 25 except that in Example 25, the compound represented by the formula (1) in Example 1 was not used. The temperature of the kneaded product when kneading was completed in Procedure 1 was 163° C.

Example 26

The measurement was performed in the same manner as in Example 20; when the unvulcanized rubber composition obtained in Reference Example 5 was used as a control, the vulcanizing rate of the unvulcanized rubber composition obtained in Procedure 2 in Example 25 was enhanced by 68%.

The result when the compound represented by the formula (1) is used is shown in Table 5. In the table, the vulcanizing rate indicates a relative value where the result of Reference Example 5 is 1.

TABLE 5

|  | Reference Example 5 | Example 26 |
| --- | --- | --- |
| Compound | — | (1) |
| Vulcanizing rate | 1 | 0.32 |

Example 27

An unvulcanized rubber composition was obtained in the same manner as in Example 25 except that in Example 25, 100 parts by weight of ethylene-propylene-diene copolymerized rubber EPDM505A (manufactured by Sumitomo Chemical Co., Ltd.) was replaced with 170 parts by weight of ethylene-propylene-diene copolymerized rubber EPDM601F (manufactured by Sumitomo Chemical Co., Ltd.). The temperature of the kneaded product when kneading was completed in Procedure 1 was 165° C.

Reference Example 6

An unvulcanized rubber composition was obtained in the same manner as in Example 27 except that in Example 27, the compound represented by the formula (1) in Example 1 was not used. The temperature of the kneaded product when kneading was completed in Procedure 1 was 159° C.

Example 28

The measurement was performed in the same manner as in Example 20; when the unvulcanized rubber composition obtained in Reference Example 6 was used as a control, the vulcanizing rate of the unvulcanized rubber composition obtained in Procedure 2 in Example 27 was enhanced by 28%.

The result when the compound represented by the formula (1) was used is shown in Table 6. In the table, the vulcanizing rate indicates a relative value when the result of Reference Example 6 is 1.

TABLE 6

|  | Reference Example 6 | Example 28 |
| --- | --- | --- |
| Compound | — | (1) |
| Vulcanizing rate | 1 | 0.72 |

Example 29

Procedure 1

Using a Banbury mixer (600-ml Labo Plastomill manufactured by Toyo Seiki Seisaku-sho, Ltd.), 100 parts by weight of ethylene-propylene-diene copolymerized rubber EPDM505A (manufactured by Sumitomo Chemical Co., Ltd.), 60 parts by weight of FEF (manufactured by Asahi Carbon Co., Ltd., trade name "Asahi #60"), 1 part by weight of stearic acid, 5 parts by weight of zinc oxide, and 1 part by weight of the compound represented by the formula (1) and obtained in Example 1 above were kneaded to obtain a kneaded product. In the step, kneading was performed at the setting temperature of the mixer of 130° C. and the number of rotations of the mixer of 50 rpm for 5 minutes after a variety of chemicals and a filler were placed. The temperature of the kneaded product when kneading was completed was 165° C.

Procedure 2

In an open roll mill in which a roll setting temperature was 60° C., the kneaded product obtained in Procedure 1, 1 part by weight of a vulcanization accelerator dibenzothiazolyl disulfide (MBTS), and 0.7 parts by weight of sulfur were kneaded and compounded to obtain an unvulcanized rubber composition.

Reference Example 7

An unvulcanized rubber composition was obtained in the same manner as in Example 29 except that in Example 29, the compound represented by the formula (1) in Example 1 was not used. The temperature of the kneaded product when kneading was completed in Procedure 1 was 163° C.

Example 30

The measurement was performed in the same manner as in Example 20; the unvulcanized rubber composition obtained in Reference Example 7 was used as a control, the vulcanizing rate of the unvulcanized rubber composition obtained in Procedure 2 in Example 29 was enhanced by 53%.

The result when the compound represented by the formula (1) was used is shown in Table 7. In the table, the vulcanizing rate indicates a relative value when the result of Reference Example 7 is 1.

TABLE 7

|  | Reference Example 7 | Example 30 |
|---|---|---|
| Compound | — | (1) |
| Vulcanizing rate | 1 | 0.47 |

Example 31

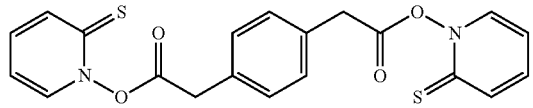

(7)

24.51 g (205.99 mmol) of thionyl chloride was added to 10.0 g (51.50 mmol) of 1,4-phenylene acetate, and was stirred for 5 hours with heating under reflux. After the reaction was completed, non-reacted thionyl chloride was distilled off under reduced pressure to obtain the target di(acid chloride) as a colorless needle. A solution (300 ml) of 11.90 g (51.50 mmol) of the resulting di(acid chloride) in chloroform was cooled to −78° C., and 13.10 g (102.99 mmol) of 2-mercaptopyridine N-oxide was added. 8.35 g (105.57 mmol) of pyridine was added dropwise at the same temperature as above, and yellow crystals were then precipitated during the process to raise the temperature to 0° C. The crystals were separated through filtration, were washed with chloroform, and were dried to obtain 12.66 g of the target bis Barton ester (2 steps, yield: 60%) represented by the above formula (7) as light yellow crystals.

$^1$H-NMR (DMF-d7, 400 MHz) δ ppm: 4.18 (4H, s), 6.92 (2H, ddd, J=6.8 Hz, 6.8 Hz, 1.7 Hz), 7.45-7.50 (6H, m), 7.61-7.64 (2H, m), 8.38-8.41 (2H, m).

Example 32

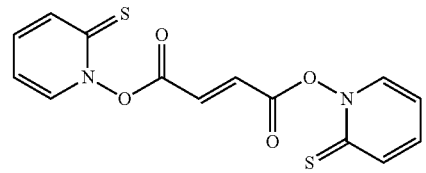

(8)

A solution (300 ml) of 10.0 g (65.38 mmol) of fumaryl chloride in chloroform was cooled to −78° C., and 16.63 g (130.75 mmol) of 2-mercaptopyridine N-oxide was added. 10.60 g (134.02 mmol) of pyridine was added dropwise at the same temperature as above; the temperature was then raised to 0° C., and stirring was performed for 1 hour. Precipitation of crystals was verified from the initial stage of the reaction. The crystals were separated through filtration, and were washed with chloroform to obtain 19.21 g of bis Barton ester (yield: 88%) represented by the above formula (8) as light yellow crystals.

$^1$H-NMR (DMF-d7, 400 MHz) δ ppm: 7.01 (2H, ddd, J=6.8 Hz, 6.8 Hz, 1.7 Hz), 7.51 (2H, s), 7.55 (2H, ddd, J=8.6 Hz, 6.8 Hz, 1.7 Hz), 7.68 (2H, dd, J=8.8 Hz, 1.7 Hz), 8.53 (2H, dd, J=7.1 Hz, 1.7 Hz).

Example 33

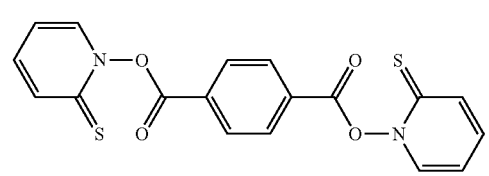

(9)

A solution (300 ml) of 10.00 g (49.26 mmol) of terephthaloyl chloride in chloroform was cooled to −78° C., and 12.53 g (98.51 mmol) of 2-mercaptopyridine N-oxide was added. 7.99 g (100.98 mmol) of pyridine was added dropwise at the same temperature as above, and yellow crystals were then precipitated during the process to raise the temperature to 0° C. The crystals were separated through filtration, were washed with chloroform, and were dried to obtain 17.75 g of the target bis Barton ester (yield: 94%) represented by the above formula (9) as light yellow crystals.

$^1$H-NMR (DMF-d7, 400 MHz) δ ppm: 7.03 (2H, ddd, J=6.8 Hz, 6.8 Hz, 2.0 Hz), 7.58 (2H, ddd, J=8.6 Hz, 6.8 Hz, 1.5 Hz), 7.69-7.71 (2H, m), 8.49 (4H, s), 8.61-8.63 (2H, m).

Example 34

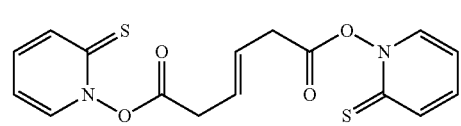

(10)

33.02 g (277.53 mmol) of thionyl chloride was added to 10.00 g (69.38 mmol) of trans-3-hexenedioic acid, and was stirred for 5 hours with heating under reflux. After the reaction was completed, non-reacted thionyl chloride was distilled off under reduced pressure to obtain the target di(acid chloride) as an oil. A solution (300 ml) of 12.50 g (69.05 mmol) of the resulting di(acid chloride) in chloroform was cooled to −78° C., and 17.56 g (138.11 mmol) of 2-mercaptopyridine N-oxide was added. 11.20 g (141.56 mmol) of pyridine was added dropwise at the same temperature as above, and the temperature was then raised to 0° C. After the reaction was completed, water was added, and extraction with chloroform, washing with saturated saline water, and drying with sodium sulfate were performed; the solvent was distilled off under reduced pressure. The resulting residue was recrystallized with THF to obtain 11.44 g of the target bis Barton ester (2 steps, yield: 44%) represented by the above formula (10) as light yellow crystals.

$^1$H-NMR (DMF-d7, 400 MHz) δ ppm: 3.64-3.65 (41H, m), 5.99-6.00 (2H, m), 6.92 (2H, ddd, J=6.8 Hz, 6.8 Hz, 1.7 Hz), 7.48 (2H, ddd, J=8.3 Hz, 6.6 Hz, 1.4 Hz), 7.60-7.63 (2H, m), 8.35-8.37 (2H, m).

Example 35

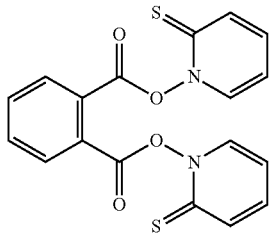

(11)

A solution (300 ml) of 10.00 g (49.26 mmol) of phthaloyl chloride in chloroform was cooled to −78° C., and 12.53 g (98.51 mmol) of 2-mercaptopyridine N-oxide was added. 7.99 g (100.98 mmol) of pyridine was added dropwise at the same temperature as above, the temperature was then raised to 0° C., and stirring was performed for 1 hour. After the reaction was completed, water was added, and extraction with chloroform, washing with saturated saline water, and drying with sodium sulfate were performed; the solvent was distilled off. The resulting residue was recrystallized with chloroform/hexane to obtain 6.7 g of the target bis Barton ester (yield: 35%) represented by the above formula (11) as light yellow crystals.

$^1$H-NMR (CDCl$_3$, 400 MHz) δ ppm: 6.68 (2H, ddd, J=3.6 Hz, 3.6 Hz, 1.4 Hz), 7.24-7.28 (2H, m), 7.72-7.75 (2H, m), 7.78-7.80 (2H, m), 7.82-7.86 (2H, m), 8.45-8.49 (2H, m).

Example 36

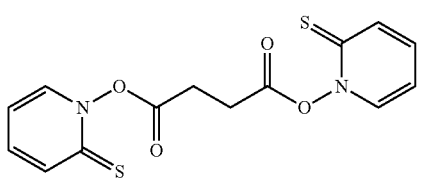

(12)

100 ml of a solution of 8.00 g (51.62 mmol) of succinyl chloride in chloroform was cooled to −78° C., and 13.13 g (103.25 mmol) of 2-mercaptopyridine N-oxide was added. 8.58 g (108.41 mmol) of pyridine was added dropwise at the same temperature as above, the temperature was then raised to 0° C., and stirring was performed for 1 hour. After the reaction was completed, the reaction was quenched with water, precipitation of crystals was verified. The crystals were separated through filtration, were washed with water and acetone in this order, and were dried to obtain 14.73 g of the target bis Barton ester (yield: 85%) represented by the above formula (12) as light yellow crystals.

$^1$H-NMR (DMSO-d6, 400 MHz) δ ppm: 3.14 (4H, s), 6.89 (2H, ddd, J=7.2 Hz, 7.2 Hz, 2.0 Hz), 7.45 (2H, ddd, J=8.0 Hz, 6.4 Hz, 1.2 Hz), 7.54-7.57 (2H, m), 8.22-8.30 (2H, m).

Example 37

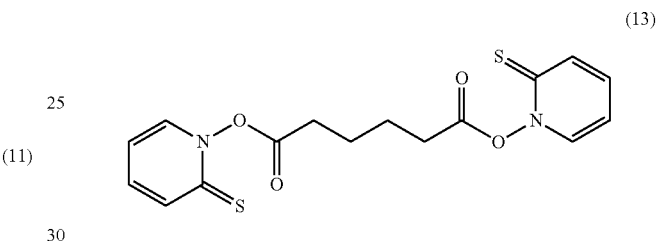

(13)

100 ml of a solution of 10.00 g (54.64 mmol) of adipoyl chloride in chloroform was cooled to −78° C., and 13.89 g (109.27 mmol) of 2-mercaptopyridine N-oxide was added. 9.08 g (114.74 mmol) of pyridine was added dropwise at the same temperature as above, the temperature was then raised to 0° C., and stirring was performed for 1 hour. After the reaction was completed, the reaction was quenched with water; extraction with chloroform, and drying with anhydrous sodium sulfate were performed; the solvent was distilled off under reduced pressure. The resulting residue was recrystallized with chloroform/hexane to obtain 17.12 g of the target bis Barton ester (yield: 86%) represented by the above formula (13) as light yellow crystals.

$^1$H-NMR (CDCl$_3$, 400 MHz) δ ppm: 1.99-2.04 (4H, m), 2.79-2.83 (4H, m), 6.65 (2H, ddd, J=6.8 Hz, 6.8 Hz, 1.6 Hz), 7.22 (2H, ddd, J=8.4 Hz, 6.8 Hz, 1.6 Hz), 7.60-7.62 (2H, m), 7.67-7.70 (2H, m).

Example 38

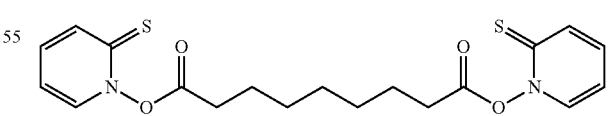

(14)

100 ml of a solution of 10.00 g (44.42 mmol) of azelaoyl chloride in chloroform was cooled to −78° C., and 11.30 g (88.85 mmol) of 2-mercaptopyridine N-oxide was added. 7.38 g (93.29 mmol) of pyridine was added dropwise at the same temperature as above, the temperature was then raised to 0° C., and stirring was performed for 1 hour. After the reaction was completed, the reaction was quenched with water, extraction with chloroform, and drying with anhydrous sodium sulfate were performed; the solvent was distilled off under reduced pressure. The resulting residue was recrystallized with chloroform/hexane to obtain 15.98 g of the target bis Barton ester (yield: 88%) represented by the above formula (14) as light yellow crystals.

$^1$H-NMR (CDCl$_3$, 400 MHz) δ ppm: 1.43-2.04 (6H, m), 1.80-1.87 (4H, m), 2.72 (4H, t, J=7.2 Hz), 6.64 (2H, ddd, J=6.8 Hz, 6.8 Hz, 1.6 Hz), 7.2 (2H, ddd, J=8.8 Hz, 6.8 Hz, 1.6 Hz), 7.57-7.60 (2H, m), 7.67-7.70 (2H, m).

Example 39

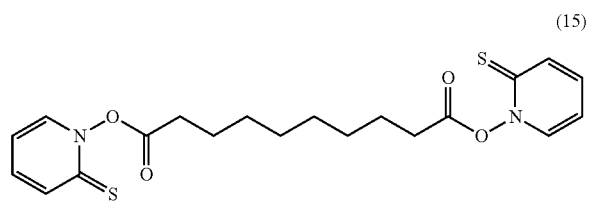 [SMILES: O=C(CCCCCCCCC(=O)On1ccccc1=S)On1ccccc1=S]

(15)

A solution of 10.00 g (41.82 mmol) of sebacoyl chloride in chloroform was cooled to −78° C., and 10.63 g (83.63 mmol) of 2-mercaptopyridine N-oxide was added. 6.95 g (87.81 mmol) of pyridine was added dropwise at the same temperature as above, the temperature was then raised to 0° C., and stirring was performed for 10 minutes. After the reaction was completed, the reaction was quenched with water; extraction with chloroform, and drying with anhydrous sodium sulfate were performed; the solvent was distilled off under reduced pressure. The resulting residue was recrystallized with chloroform/hexane to obtain 18.84 g of the target bis Barton ester (>99%) represented by the above formula (15) as light yellow crystals.

$^1$H-NMR (CDCl3, 400 MHz) δ ppm: 1.36-1.49 (8H, m), 1.79-1.86 (4H, m), 2.72 (4H, t, J=7.6 Hz), 6.63 (2H, ddd, J=8.4 Hz, 6.8 Hz, 1.6 Hz), 7.21 (2H, ddd, J=8.4 Hz, 6.8 Hz, 1.6 Hz), 7.56-7.58 (2H, m), 7.67-7.70 (2H, m).

Example 40

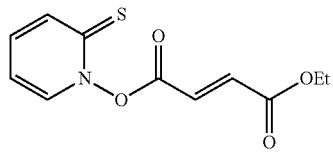

(16)

4.40 g (34.69 mmol) of oxalyl chloride and a small amount of DMF were added to 400 ml of a solution of 5.00 g (34.69 mmol) of fumaric acid monoethyl ester in chloroform, and were stirred under the condition of room temperature for 2 hours. The reaction solution was cooled to −78° C., and 4.41 g (34.69 mmol) of 2-mercaptopyridine N-oxide was added. 6.86 g (86.73 mmol) of pyridine was added dropwise over 5 minutes at the same temperature as above; the temperature was raised to room temperature, and stirring was then performed for 10 minutes. After the reaction was completed, water was added; extraction with chloroform, washing with saturated saline water, and drying with sodium sulfate were performed; the solvent was distilled off. The resulting residue was refined by silica gel column chromatography (70% ethyl acetate/hexane) to obtain 5.25 g of the target bis Barton ester (yield: 63%) represented by the above formula (16) as a dark yellow oil.

$^1$H-NMR (CDCl$_3$, 270 MHz) δ ppm: 1.34 (3H, t, J=7.3), 4.31 (2H, q, J=7.3), 6.68 (1H, ddd, J=6.9 Hz, 6.9 Hz, 1.6 Hz), 7.10 (1H, d, J=15.8 Hz), 7.20 (1H, d, J=15.8 Hz), 7.19-7.28 (1H, m), 7.64-7.66 (1H, m), 7.67-7.73 (1H, m).

Example 41

Procedure 1

Using a Banbury mixer (600-ml Labo Plastomill manufactured by Toyo Seiki Seisaku-sho, Ltd.), 100 parts by weight of natural rubber (RSS#1), 45 parts by weight of HAF (manufactured by Asahi Carbon Co., Ltd., trade name "Asahi #70"), 3 parts by weight of stearic acid, 5 parts by weight of zinc oxide, 1 part by weight of an antioxidant (N-phenyl-N'-1,3-dimethylbutyl-p-phenylenediamine (6PPD): trade name "Antigen (registered trademark) 6C" manufactured by Sumitomo Chemical Co., Ltd.), and 1 part by weight of the compound represented by the formula (7) and obtained in Example 31 above were kneaded to obtain a kneaded product. In the step, kneading was performed at the setting temperature of the mixer of 120° C. and the number of rotations of the mixer of 50 rpm for 5 minutes after a variety of chemicals and a filler were placed. The temperature of the kneaded product when kneading was completed was 165° C.

Procedure 2

In an open roll mill in which a roll setting temperature was 60° C., the kneaded product obtained in Procedure 1, 1 part by weight of a vulcanization accelerator N-cyclohexyl-2-benzothiazolesulfenamide (CBS), and 2 parts by weight of sulfur were kneaded and compounded to obtain an unvulcanized rubber composition.

Reference Example 8

An unvulcanized rubber composition was obtained in the same manner as in Example 41 except that in Example 41, the compound represented by the formula (7) was not used. The temperature of the kneaded product when kneading was completed in Procedure 1 was 164° C.

Example 42

As described below, the vulcanization curve of the unvulcanized rubber composition obtained in Procedure 2 in Example 41 was measured, and the vulcanizing rate and the reversion rate were calculated.
(1) Vulcanization Curve
The vulcanization curve was measured with a rotorless rheometer RLR-4 manufactured by Toyo Seiki Seisaku-sho, Ltd.
Conditions: temperature: 145° C. (vulcanizing rate), 190° C. (reversion rate)
angle of vibration: 1.0 deg., the number of vibrations: 100 cpm
(2) Vulcanizing Rate
From the result obtained from (1), the vulcanizing rate was calculated from the expression (50) using a time to reach 10% vulcanization (T10) and a time to reach 90% vulcanization (T90). A smaller value indicates the time from the start of vulcanization to the end thereof is shorter, unevenness of vulcanization is barely generated, and vulcanization properties are higher.

vulcanizing rate (min)=T90 (min)−T10 (min)　　expression (50)

(3) Reversion Rate

From the result obtained from (1), the torque increasing value (M(15)−ML) after 15 minutes from the start of vulcanization was expressed as a relative value to the torque increasing value (MH−ML), which was defined as 100, and the reversion rate was determined as a value obtained by subtracting the torque increasing value (M(15)−ML) from 100. A smaller value indicates that reversion is more reduced, and vulcanization properties are higher.

reversion rate=100−{[M(15)−ML]/[MH−ML]}×100

When the unvulcanized rubber composition obtained in Reference Example 8 was used as a control, the vulcanizing rate of the unvulcanized rubber composition obtained in Procedure 2 in Example 41 was enhanced by 24%, and the reversion rate was reduced by 18 points.

Example 43

An unvulcanized rubber composition was obtained in the same manner as in Example 41 except that in Example 41, the compound represented by the formula (7) in Example 31 was replaced with the compound represented by the formula (8) in Example 32. The temperature of the kneaded product when kneading was completed in Procedure 1 was 165° C.

Example 44

The measurement was performed in the same manner as in Example 42; when the unvulcanized rubber composition obtained in Reference Example 8 was used as a control, the vulcanizing rate of the unvulcanized rubber composition obtained in Procedure 2 in Example 43 was enhanced by 22%, and the reversion rate was reduced by 16 points.

Example 45

An unvulcanized rubber composition was obtained in the same manner as in Example 41 except that in Example 41, the compound represented by the formula (7) in Example 31 was replaced with the compound represented by the formula (9) in Example 33. The temperature of the kneaded product when kneading was completed in Procedure 1 was 163° C.

Example 46

The measurement was performed in the same manner as in Example 42; when the unvulcanized rubber composition obtained in Reference Example 8 was used as a control, the vulcanizing rate of the unvulcanized rubber composition obtained in Procedure 2 in Example 45 was enhanced by 17%, and the reversion rate was reduced by 19 points.

Example 47

An unvulcanized rubber composition was obtained in the same manner as in Example 41 except that in Example 41, the compound represented by the formula (7) in Example 31 was replaced with the compound represented by the formula (10) in Example 34. The temperature of the kneaded product when kneading was completed in Procedure 1 was 165° C.

Example 48

The measurement was performed in the same manner as in Example 42; when the unvulcanized rubber composition obtained in Reference Example 8 was used as a control, the vulcanizing rate of the unvulcanized rubber composition obtained in Procedure 2 in Example 47 was enhanced by 29%, and the reversion rate was reduced by 20 points.

Example 49

An unvulcanized rubber composition was obtained in the same manner as in Example 41 except that in Example 41, the compound represented by the formula (7) in Example 31 was replaced with the compound represented by the formula (11) in Example 35. The temperature of the kneaded product when kneading was completed in Procedure 1 was 166° C.

Example 50

The measurement was performed in the same manner as in Example 42; when the unvulcanized rubber composition obtained in Reference Example 8 was used as a control, the vulcanizing rate of the unvulcanized rubber composition obtained in Procedure 2 in Example 49 was enhanced by 23%, and the reversion rate was reduced by 18 points.

The results when the compounds represented by the formulae (7) to (11) were used are shown in Table 8. In the table, the vulcanizing rate and the reversion rate indicate relative values where the results of Reference Example 8 are 1.

TABLE 8

|  | Reference Example 8 | Example 42 | Example 44 | Example 46 | Example 48 | Example 50 |
|---|---|---|---|---|---|---|
| Compound | — | (7) | (8) | (9) | (10) | (11) |
| Vulcanizing rate | 1 | 0.76 | 0.78 | 0.83 | 0.71 | 0.77 |
| Reversion rate | 1 | 0.61 | 0.65 | 0.59 | 0.58 | 0.61 |

Example 51

Procedure 1

Using a Banbury mixer (600-ml Labo Plastomill manufactured by Toyo Seiki Seisaku-sho, Ltd.), 100 parts by weight of natural rubber (RSS#1), 45 parts by weight of HAF (manufactured by Asahi Carbon Co., Ltd., trade name "Asahi #70"), 3 parts by weight of stearic acid, 5 parts by weight of zinc oxide, 1 part by weight of an antioxidant (N-phenyl-N'-1,3-dimethylbutyl-p-phenylenediamine (6PPD): trade name "Antigen (registered trademark) 6C" manufactured by Sumitomo Chemical Co., Ltd.), and 1 part by weight of the compound represented by the formula (12) and obtained in Example 34 above were kneaded to obtain a kneaded product. In the step, kneading was performed at the setting temperature of the mixer of 120° C. and the number of rotations of the mixer of 50 rpm for 5 minutes after a variety of chemicals and a filler were placed. The temperature of the kneaded product when kneading was completed was 164° C.

Procedure 2

In an open roll mill in which a roll setting temperature was 60° C., the kneaded product obtained in Procedure 1, 1 part by weight of a vulcanization accelerator N-cyclohexyl-2- benzothiazolesulfenamide (CBS), and 2 parts by weight of sulfur were kneaded and compounded to obtain an unvulcanized rubber composition.

Reference Example 9

An unvulcanized rubber composition was obtained in the same manner as in Example 51 except that in Example 51, the compound represented by the formula (12) was not used. The temperature of the kneaded product when kneading was completed in Procedure 1 was 165° C.

Example 52

As described below, the vulcanization curve of the unvulcanized rubber composition obtained in Procedure 2 in Example 51 was measured, and the vulcanizing rate and the reversion rate were calculated.
(1) Vulcanization Curve
The vulcanization curve was measured with a rotorless rheometer RLR-4 manufactured by Toyo Seiki Seisaku-sho, Ltd.
Conditions: temperature: 145° C. (vulcanizing rate), 190° C. (reversion rate)
angle of vibration: 1.0 deg., the number of vibrations: 100 cpm
(2) Vulcanizing Rate
From the result obtained from (1), the vulcanizing rate was calculated from the expression (50) using a time to reach 10% vulcanization (T10) and a time to reach 90% vulcanization (T90). A smaller value indicates the time from the start of vulcanization to the end thereof is shorter, unevenness of vulcanization is barely generated, and vulcanization properties are higher.

vulcanizing rate (min)=$T$90 (min)−$T$10 (min)    expression (50)

(3) Reversion Rate
From the result obtained from (1), the torque increasing value (M(15)−ML) after 15 minutes from the start of vulcanization was expressed as a relative value to the torque increasing value (MH−ML), which was defined as 100, and the reversion rate was determined as a value obtained by subtracting the torque increasing value (M(15)−ML) from 100. A smaller value indicates that reversion is more reduced, and vulcanization properties are higher.

reversion rate=100−{[$M$(15)−$ML$]/[$MH$−$ML$]}×100

When the unvulcanized rubber composition obtained in Reference Example 9 was used as a control, the vulcanizing rate of the unvulcanized rubber composition obtained in Procedure 2 in Example 51 was enhanced by 30%, and the reversion rate was reduced by 24 points.

Example 53

An unvulcanized rubber composition was obtained in the same manner as in Example 51 except that in Example 51, the compound represented by the formula (12) in Example 36 was replaced with the compound represented by the formula (13) in Example 37. The temperature of the kneaded product when kneading was completed in Procedure 1 was 165° C.

Example 54

The measurement was performed in the same manner as in Example 52; when the unvulcanized rubber composition obtained in Reference Example 9 was used as a control, the vulcanizing rate of the unvulcanized rubber composition obtained in Procedure 2 in Example 53 was enhanced by 39%, and the reversion rate was reduced by 18 points.

Example 55

An unvulcanized rubber composition was obtained in the same manner as in Example 51 except that in Example 51, the compound represented by the formula (12) in Example 36 was replaced with the compound represented by the formula (14) in Example 38. The temperature of the kneaded product when kneading was completed in Procedure 1 was 165° C.

Example 56

The measurement was performed in the same manner as in Example 52; when the unvulcanized rubber composition obtained in Reference Example 9 was used as a control, the vulcanizing rate of the unvulcanized rubber composition obtained in Procedure 2 in Example 55 was enhanced by 38%, and the reversion rate was reduced by 19 points.

Example 57

An unvulcanized rubber composition was obtained in the same manner as in Example 51 except that in Example 51, the compound represented by the formula (12) in Example 36 was replaced with the compound represented by the formula (15) in Example 39. The temperature of the kneaded product when kneading was completed in Procedure 1 was 164° C.

Example 58

The measurement was performed in the same manner as in Example 52; when the unvulcanized rubber composition obtained in Reference Example 9 was used as a control, the vulcanizing rate of the unvulcanized rubber composition obtained in Procedure 2 in Example 57 was enhanced by 41%, and the reversion rate was reduced by 19 points.

Example 59

An unvulcanized rubber composition was obtained in the same manner as in Example 51 except that in Example 51, the compound represented by the formula (12) in Example 36 was replaced with the compound represented by the formula (16) in Example 40. The temperature of the kneaded product when kneading was completed in Procedure 1 was 165° C.

Example 60

The measurement was performed in the same manner as in Example 52; when the unvulcanized rubber composition obtained in Reference Example 9 was used as a control, the vulcanizing rate of the unvulcanized rubber composition obtained in Procedure 2 in Example 59 was enhanced by 30%, and the reversion rate was reduced by 17 points.

The results when the compounds represented by the formulae (12) to (16) were used are shown in Table 9. In the table, the vulcanizing rate and the reversion rate indicate relative values where the results of Reference Example 9 are 1.

TABLE 9

| | Reference Example 9 | Example 52 | Example 54 | Example 56 | Example 58 | Example 60 |
|---|---|---|---|---|---|---|
| Compound | — | (12) | (13) | (14) | (15) | (16) |
| Vulcanizing rate | 1 | 0.70 | 0.61 | 0.62 | 0.59 | 0.70 |
| Reversion rate | 1 | 0.48 | 0.62 | 0.58 | 0.58 | 0.64 |

Example 61

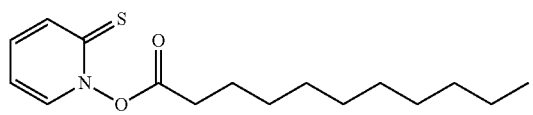

(17)

A solution of 9.20 g (44.94 mmol) of stearoyl chloride in chloroform was cooled to −78° C., and 5.71 g (3.63 mmol) of 2-mercaptopyridine N-oxide was added. 3.63 g (45.83 mmol) of pyridine was added dropwise at the same temperature as above, the temperature was then raised to 0° C., and stirring was performed for 1 hour. After the reaction was completed, the reaction was quenched with water; extraction with chloroform, washing with brine, and drying with anhydrous sodium sulfate were performed; the solvent was distilled off under reduced pressure. The resulting residue was recrystallized with ethyl acetate/hexane to obtain 5.75 g of the target mono Barton ester (43%) represented by the above formula (17) as light yellow crystals.

$^1$H-NMR (CDCl3, 400 MHz) δ ppm: 0.88 (3H, t, J=6.8 Hz), 1.24-1.36 (12H, m), 1.40-1.47 (2H, m), 1.78-1.85 (2H, m), 2.71 (2H, t, J=7.8 Hz), 6.63 (2H, ddd, J=8.6 Hz, 6.9 Hz, 1.7 Hz), 7.21 (2H, ddd, J=8.6 Hz, 6.9 Hz, 1.7 Hz), 7.55-7.57 (2H, m), 7.68-7.70 (2H, m).

Example 62

Procedure 1

Using a Banbury mixer (600-ml Labo Plastomill manufactured by Toyo Seiki Seisaku-sho, Ltd.), 100 parts by weight of natural rubber (RSS#1), 45 parts by weight of HAF (manufactured by Asahi Carbon Co., Ltd., trade name "Asahi #70"), 3 parts by weight of stearic acid, 5 parts by weight of zinc oxide, 1 part by weight of an antioxidant (N-phenyl-N'-1,3-dimethylbutyl-p-phenylenediamine (6PPD): trade name "Antigen (registered trademark) 6C" manufactured by Sumitomo Chemical Co., Ltd.), and 1 part by weight of the compound represented by the formula (17) and obtained in Example 61 above were kneaded to obtain a kneaded product. In the step, kneading was performed at the setting temperature of the mixer of 120° C. and the number of rotations of the mixer of 50 rpm for 5 minutes after a variety of chemicals and a filler were placed. The temperature of the kneaded product when kneading was completed was 164° C.

Procedure 2

In an open roll mill in which a roll setting temperature was 60° C., the kneaded product obtained in Procedure 1, 1 part by weight of a vulcanization accelerator N-cyclohexyl-2-benzothiazolesulfenamide (CBS), and 2 parts by weight of sulfur were kneaded and compounded to obtain an unvulcanized rubber composition.

Reference Example 10

An unvulcanized rubber composition was obtained in the same manner as in Example 62 except that in Example 62, the compound represented by the formula (17) was not used. The temperature of the kneaded product when kneading was completed in Procedure 1 was 164° C.

Example 63

As described below, the vulcanization curve of the unvulcanized rubber composition obtained in Procedure 2 in Example 62 was measured, and the vulcanizing rate and the reversion rate were calculated.

(1) Vulcanization Curve

The vulcanization curve was measured with a rotorless rheometer RLR-4 manufactured by Toyo Seiki Seisaku-sho, Ltd.

Conditions: temperature: 145° C. (vulcanizing rate), 190° C. (reversion rate)

angle of vibration: 1.0 deg., the number of vibrations: 100 cpm (2) Vulcanizing Rate From the result obtained from (1), the vulcanizing rate was calculated from the expression (50) using a time to reach 10% vulcanization (T10) and a time to reach 90% vulcanization (T90). A smaller value indicates the time from the start of vulcanization to the end thereof is shorter, unevenness of vulcanization is barely generated, and vulcanization properties are higher.

vulcanizing rate (min)=$T$90 (min)−$T$10 (min)    expression (50)

(3) Reversion Rate

From the result obtained from (1), the torque increasing value (M(15)−ML) after 15 minutes from the start of vulcanization was expressed as a relative value to the torque increasing value (MH−ML), which was defined as 100, and the reversion rate was determined as a value obtained by subtracting the torque increasing value (M(15)−ML) from 100. A smaller value indicates that reversion is more reduced, and vulcanization properties are higher.

reversion rate=100−{[$M$(15)−$ML$]/[$MH$−$ML$]}×100

When the unvulcanized rubber composition obtained in Reference Example 10 was used as a control, the vulcanizing rate of the unvulcanized rubber composition obtained in Procedure 2 in Example 62 was enhanced by 27%, and the reversion rate was reduced by 17 points.

The results when the compound represented by the formula (17) was used are shown in Table 10. In the table, the vulcanizing rate and the reversion rate indicate relative values where the results of Reference Example 10 are 1.

TABLE 10

| | Reference Example 10 | Example 63 |
|---|---|---|
| Compound | — | (17) |
| Vulcanizing rate | 1 | 0.73 |
| Reversion rate | 1 | 0.64 |

INDUSTRIAL APPLICABILITY

The rubber composition according to the present invention is useful because the vulcanizing rate of the rubber component is high.

The invention claimed is:

1. A rubber composition comprising a compound having one or more groups represented by formula (X), and a rubber component:

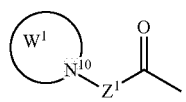

(X)

wherein ring $W^1$ represents a cyclic group having one —C(=O)— or one —C(=S)—; $N^{10}$ represents a nitrogen atom; the at least one selected from the group consisting of —C(=O)— and —C(=S)— in the ring $W^1$ and $N^{10}$ are conjugated; and $Z^1$ represents —O— or —S—.

2. The rubber composition according to claim 1, wherein the ring $W^1$ is a 5-membered ring, a 6-membered ring, or a 7-membered ring.

3. The rubber composition according to claim 1, wherein the ring $W^1$ is a cyclic group composed of $N^{10}$ and four, five, or six carbon atoms,
one or more of the carbon atoms may be replaced with —O—, —NH—, —S—, or =N—, and
the carbon atoms and —NH—.

4. The rubber composition according to claim 1, wherein the one —C(=O)— or the one —C(=S)— is bonded to $N^{10}$.

5. The rubber composition according to claim 1, wherein the compound having one or more groups represented by the formula (X) is a compound having two or more groups represented by the formula (X).

6. The rubber composition according to claim 1, wherein the compound having one or more groups represented by the formula (X) is a compound represented by formula (I):

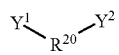

(I)

wherein $Y^1$ represents a group represented by the formula (X); $Y^2$ represents a hydrogen atom, a group represented by the formula (X), or a group represented by formula (b); and $R^{20}$ represents a divalent hydrocarbon group;

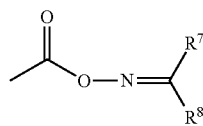

(b)

wherein $R^7$ and $R^8$ each independently represent a hydrogen atom, an alkyl group having 1 to 12 carbon atoms, an aryl group having 6 to 20 carbon atoms, or an aralkyl group having 7 to 18 carbon atoms, or $R^7$ and $R^8$ are bonded to each other to form a ring together with a carbon atom bonded by $R^7$ and $R^8$.

7. The rubber composition according to claim 6, wherein $Y^2$ is a group represented by the formula (X) or a group represented by the formula (b).

8. The rubber composition according to claim 6, wherein $Y^2$ is a hydrogen atom, and $R^{20}$ is an alkanediyl group having 1 to 18 carbon atoms.

9. The rubber composition according to claim 1, wherein the compound having one or more groups represented by the formula (X) is a compound represented by formula (A1):

(A1)

wherein $Y^1$ represents a group represented by the formula (X); and $R^9$ represents an alkyl group having 1 to 12 carbon atoms.

10. The rubber composition according to claim 1, further comprising a sulfur component.

11. A vulcanized rubber obtained through a heat treatment of the rubber composition according to claim 10.

12. A tire including a rubber member comprising a vulcanized rubber obtained through a heat treatment of the rubber composition according to claim 10.

13. A vulcanization aid comprising a compound represented by formula (A2):

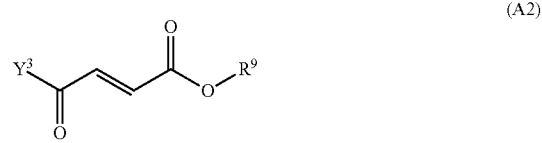

(A2)

wherein $Y^3$ represents a group represented by the formula (W):

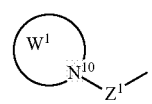

(W)

wherein ring $W^1$ has at least one selected from the group consisting of —C(=O)— and —C(=S)—; $N^{10}$ represents a nitrogen atom; the at least one selected from the group consisting of —C(=O)— and —C(=S)— in the ring $W^1$ and $N^{10}$ are conjugated; and $Z^1$ represents —O— or —S—; and $R^9$ represents an alkyl group having 1 to 12 carbon atoms.

* * * * *